(12) United States Patent
Ovokaitys

(10) Patent No.: US 12,246,037 B2
(45) Date of Patent: Mar. 11, 2025

(54) METHODS AND SYSTEMS FOR INCREASED PRODUCTION OF STEM CELLS

(71) Applicant: Todd Frank Ovokaitys, Carlsbad, CA (US)

(72) Inventor: Todd Frank Ovokaitys, Carlsbad, CA (US)

( * ) Notice: Subject to any disclaimer, the term of this patent is extended or adjusted under 35 U.S.C. 154(b) by 402 days.

(21) Appl. No.: 17/643,279

(22) Filed: Dec. 8, 2021

(65) Prior Publication Data

US 2022/0175832 A1    Jun. 9, 2022

Related U.S. Application Data

(60) Provisional application No. 63/180,742, filed on Apr. 28, 2021, provisional application No. 63/122,836, (Continued)

(51) Int. Cl.
*A61K 35/16*      (2015.01)
*A61K 35/19*      (2015.01)
(Continued)

(52) U.S. Cl.
CPC .............. *A61K 35/16* (2013.01); *A61K 35/19* (2013.01); *A61M 1/3693* (2013.01);
(Continued)

(58) Field of Classification Search
CPC ...... A61K 35/16; A61K 35/19; A61K 35/545; A61K 41/00; A61K 2236/53; A61M 1/3693; A61M 2202/0415; A61M 2202/0427; A61M 1/3681; A61M 1/3695; B01D 21/262; B01D 21/26; B01D 17/0217
See application file for complete search history.

(56) References Cited

U.S. PATENT DOCUMENTS

| | | | |
|---|---|---|---|
| 3,703,576 A | 11/1972 | Kitajima | |
| 4,840,174 A | 6/1989 | Gluckman | |

(Continued)

FOREIGN PATENT DOCUMENTS

| | | | | |
|---|---|---|---|---|
| AU | 2010244047 A1 | * | 11/2011 | ............. A61K 35/12 |
| AU | 2013206755 A1 | * | 9/2014 | ............. A61K 35/28 |

(Continued)

OTHER PUBLICATIONS

Sanchez-Gonzalez et al publication: "Platelet-Rich Plasma Peptides: Key for Regeneration", Published by International Journal of Peptides, vol. 2012, Article ID 532519, published 2012. (Year: 2012).*

(Continued)

*Primary Examiner* — Joseph W Drodge
(74) *Attorney, Agent, or Firm* — Novel IP

(57) ABSTRACT

Platelet rich plasma containing human very small embryonic-like stem cells (hVSEL) is treated with amplitude-modulated pulses of laser light having a predefined wavelength for a predefined time period, where the predefined wavelength ranges from 300 nm to 1000 nm. Treatment of the platelet rich plasma using this method results in an unexpectedly high degree of proliferation of the hVSEL in the platelet rich plasma, resulting in reduction of biological age, when administered to a patient.

16 Claims, 14 Drawing Sheets

Related U.S. Application Data filed on Dec. 8, 2020, provisional application No. 63/122,831, filed on Dec. 8, 2020.

(51) Int. Cl.
   *A61M 1/36*     (2006.01)
   *B01D 21/26*    (2006.01)

(52) U.S. Cl.
   CPC .............. *A61M 2202/0415* (2013.01); *A61M 2202/0427* (2013.01); *B01D 21/262* (2013.01)

(56) References Cited

U.S. PATENT DOCUMENTS

| | | | |
|---|---|---|---|
| 5,571,797 A | 11/1996 | Ohno | |
| 5,874,266 A | 2/1999 | Palsson | |
| 6,064,500 A | 5/2000 | Strachan | |
| 6,763,607 B2 | 7/2004 | Beyerinck | |
| 6,811,564 B1 | 11/2004 | Strachan | |
| 7,294,508 B2 | 11/2007 | Parikh | |
| 7,427,502 B2 | 9/2008 | Gostjeva | |
| 7,674,620 B2 | 3/2010 | Totey | |
| 7,829,335 B2 | 11/2010 | Inoue | |
| 8,173,632 B2 | 5/2012 | Ovokaitys | |
| 8,313,477 B2 | 11/2012 | See | |
| 8,377,989 B2 | 2/2013 | Ovokaitys | |
| 8,404,733 B2 | 3/2013 | Ovokaitys | |
| 8,748,178 B2 | 6/2014 | Egli | |
| 8,788,213 B2 | 7/2014 | Bright | |
| 9,999,785 B2 * | 6/2018 | Ovokaitys | A61N 5/0622 |
| 10,202,598 B2 * | 2/2019 | Ovokaitys | A61K 41/0023 |
| 10,907,144 B2 * | 2/2021 | Ovokaitys | A61N 5/0622 |
| 2001/0005586 A1 | 6/2001 | Palsson | |
| 2002/0034546 A1 | 3/2002 | Ullah | |
| 2002/0058952 A1 | 5/2002 | Weber | |
| 2002/0164790 A1 | 11/2002 | Warburton | |
| 2003/0163931 A1 | 9/2003 | Beyerinck | |
| 2004/0071786 A1 | 4/2004 | Grippi | |
| 2004/0204746 A1 | 10/2004 | Ovokaitys | |
| 2004/0230257 A1 | 11/2004 | Ovokaitys | |
| 2004/0239044 A1 | 12/2004 | Blatter | |
| 2004/0247671 A1 | 12/2004 | Prescott | |
| 2005/0170506 A1 | 8/2005 | Sayre | |
| 2005/0188921 A1 | 9/2005 | Malone | |
| 2006/0013869 A1 | 1/2006 | Ignatious | |
| 2006/0129210 A1 | 6/2006 | Cantin | |
| 2007/0003615 A1 | 1/2007 | Jenkins | |
| 2007/0154465 A1 | 7/2007 | Kharazi | |
| 2007/0231307 A1 | 10/2007 | Tankovich | |
| 2008/0064099 A1 | 3/2008 | Parikh | |
| 2008/0117416 A1 | 5/2008 | Hunter | |
| 2008/0118477 A1 | 5/2008 | Christopherson | |
| 2008/0176332 A1 | 7/2008 | Berns | |
| 2008/0183162 A1 | 7/2008 | Altshuler | |
| 2008/0199513 A1 | 8/2008 | Beretta | |
| 2009/0131376 A1 | 5/2009 | Ovokaitys | |
| 2009/0131710 A1 | 5/2009 | Ovokaitys | |
| 2010/0015576 A1 | 1/2010 | Altshuler | |
| 2010/0068141 A1 | 3/2010 | Kaushal | |
| 2010/0196497 A1 * | 8/2010 | Lim | A61K 35/16 424/530 |
| 2010/0209396 A1 | 8/2010 | Daley | |
| 2011/0132818 A1 * | 6/2011 | Dopslaff | B01J 47/14 210/96.1 |
| 2011/0144011 A1 | 6/2011 | McCarthy | |
| 2012/0041521 A1 | 2/2012 | Oron | |
| 2012/0101479 A1 | 4/2012 | Paspaliaris | |
| 2012/0129158 A1 | 5/2012 | Berns | |
| 2012/0171180 A1 * | 7/2012 | Abramson | A61P 11/06 424/93.72 |
| 2012/0215156 A1 | 8/2012 | Ishikawa | |
| 2012/0220641 A1 | 8/2012 | Ovokaitys | |
| 2012/0258451 A1 | 10/2012 | Klimanskaya | |
| 2014/0004601 A1 | 1/2014 | Lim | |
| 2014/0093482 A1 | 4/2014 | Paspaliaris | |
| 2014/0128800 A1 | 5/2014 | Kim | |
| 2014/0200503 A1 | 7/2014 | Centurion | |
| 2014/0273207 A1 | 9/2014 | Chan | |
| 2014/0303546 A1 | 10/2014 | Badiavas | |
| 2014/0377831 A1 | 12/2014 | Ho | |
| 2015/0343234 A1 | 12/2015 | Ovokaitys | |
| 2015/0353433 A1 | 12/2015 | Ovokaitys | |
| 2016/0040131 A1 | 2/2016 | Imran | |
| 2017/0233717 A1 * | 8/2017 | Ovokaitys | A61K 41/0023 604/20 |
| 2017/0313983 A1 | 11/2017 | Crawford | |
| 2019/0382750 A1 | 12/2019 | Ovokaitys | |
| 2020/0316116 A1 | 10/2020 | Miller, IV | |
| 2020/0338039 A1 * | 10/2020 | Niedernhofer | C12Q 1/6876 |
| 2020/0384033 A1 | 12/2020 | Morawa | |
| 2021/0207121 A1 | 7/2021 | Ovokaitys | |
| 2021/0228644 A1 | 7/2021 | Reidling | |
| 2022/0011321 A1 | 1/2022 | Rolfs | |
| 2022/0175832 A1 | 6/2022 | Ovokaitys | |
| 2022/0211770 A1 | 7/2022 | Toleikis | |

FOREIGN PATENT DOCUMENTS

| | | | |
|---|---|---|---|
| CN | 1046936 A | 11/1990 | |
| CN | 101663066 A | 3/2010 | |
| CN | 108472417 A * | 8/2018 | A61K 35/28 |
| CN | 109517786 A * | 3/2019 | A61K 35/14 |
| EP | 1011697 | 6/2000 | |
| EP | 1292134 A2 | 3/2003 | |
| EP | 1421181 | 5/2004 | |
| EP | 1892290 | 2/2008 | |
| EP | 2248888 | 11/2010 | |
| EP | 3047864 A1 * | 7/2016 | A61M 1/029 |
| JP | H0549483 A | 3/1993 | |
| JP | 2008194055 | 8/2008 | |
| JP | 2012100599 A | 5/2012 | |
| JP | 2015186465 A | 10/2015 | |
| JP | 2015223453 A * | 12/2015 | A61B 18/24 |
| RU | 2291703 | 1/2007 | |
| SG | 172471 | 7/2011 | |
| WO | 1995029645 | 2/1995 | |
| WO | 1996039489 | 2/1996 | |
| WO | 1998042356 | 2/1998 | |
| WO | 0100563 A1 | 1/2001 | |
| WO | 2001068110 | 1/2001 | |
| WO | 02059087 A1 | 8/2002 | |
| WO | 2003018783 | 1/2003 | |
| WO | 2003029402 | 1/2003 | |
| WO | 03020291 A1 | 3/2003 | |
| WO | 2004071435 A2 | 8/2004 | |
| WO | 2004081172 | 9/2004 | |
| WO | 2007014323 | 2/2007 | |
| WO | 2007051170 A3 | 5/2007 | |
| WO | 2007100614 | 9/2007 | |
| WO | 2008013985 A2 | 1/2008 | |
| WO | 2008089292 | 7/2008 | |
| WO | 2009050696 | 4/2009 | |
| WO | 2009052246 A1 | 4/2009 | |
| WO | 2009052248 A1 | 4/2009 | |
| WO | 2010005557 | 1/2010 | |
| WO | 2010124585 | 11/2010 | |
| WO | 2010134007 | 11/2010 | |
| WO | 2011100651 A1 | 8/2011 | |
| WO | 2011109797 | 9/2011 | |
| WO | 2012071393 | 5/2012 | |
| WO | 2012122081 A2 | 9/2012 | |
| WO | 2012131558 | 10/2012 | |
| WO | 2012178156 | 12/2012 | |
| WO | 2013003557 A1 | 1/2013 | |
| WO | 2013063406 | 5/2013 | |
| WO | 2013141715 A1 | 9/2013 | |
| WO | 2014185945 | 11/2014 | |
| WO | 2015053694 | 4/2015 | |
| WO | 2015184421 A1 | 12/2015 | |
| WO | 2015187974 A1 | 12/2015 | |
| WO | 2017083755 A1 | 5/2017 | |
| WO | WO-2019126557 A1 * | 6/2019 | A01N 1/0205 |

(56) References Cited

FOREIGN PATENT DOCUMENTS

| WO | 2020242971 A1 | 12/2020 |
|---|---|---|
| WO | 2021021919 A1 | 2/2021 |
| WO | 2022126109 A1 | 6/2022 |

OTHER PUBLICATIONS

Arnable et al publication: "Platelet-rich plasma preparation for regenerative medicine: optimzation and quantification of cytokines and growth factors", Published in Stem Cell Research & Therapy, vol. 4:67, published 2013. (Year: 2013).*
English Translation of Patent Publication JP-2015223453-A, published Dec. 14, 2015. (Year: 2015).*
English Translation of Patent Publication CN-108472417-A, published Aug. 31, 2018. (Year: 2018).*
Li et al, "Frontiers: Progress in biological age research", Published in a Review Article of Front. Public Health, vol. 11, Aging and Public Health Section, Apr. 11, 2023. (Year: 2023).*
English Translation of Mai et al Patent Publication CN 109517786A, published Mar. 26, 2019. (Year: 2019).*
Hollands Peter et al: "The action of modulated laser light on Human Very Small Embryoni-Like (hVESL) stem cells in Platelet Rich Plasma (PRP)", CellR4, Dec. 7, 2020 (Dec. 7, 2020), pp. 1-11, XP093207471, DOI: 10.32113/cellr4_202012_2990; Retrieved from the Internet: URL:https://www.cellr4.org/wp-content/uploads/sites/2/2020/12/e2990.pdf.
Bhartiya, D. (2017). Shifting gears from embryonic to very small embryonic-like stem cells for regenerative medicine. Indian J. Med. Res. 146: 15-21.
Burd A, Zhu N, Poon VK. A study of Q-switched Nd:YAG laser irradiation and paracrine function in human skin cells (2005). Photodermatol Photoimmunol Photomed. 21(3):131-137. doi:10.1111/j.1600-0781.2005.00155.x.
Emelyanov, A.N. & Kiryanova, V.V. (2015). Photomodulation of proliferation and differentiation of stem cells by the visible and infrared light. Photomed. Laser Surg 33: 164-174.
Fekrazad, R., Asefi, S., Allahdadi, M. & Kalhori, K.A. (2016). Effect of Photobiomodulation on Mesenchymal Stem Cells. Photomed. Laser Surg. 34: 533-542.
Ginani, F., Soares, D.M., de Oliveira Rocha, H.A., et al. (2018). Low-level laser irradiation induces in vitro proliferation of stem cells from human exfoliated deciduous teeth. Lasers med. Sci. 33: 95-102.
Guerin CL, Blandinières A, Planquette B, et al. (2017). Very Small Embryonic-like Stem Cells Are Mobilized in Human Peripheral Blood during Hypoxemic COPD Exacerbations and Pulmonary Hypertension. Stem Cell Rev Rep. 13(4): 561-566. doi:10.1007/s12015-017-9732-6.
Josselyn, S.A. (2018). The past, present and future of light-gated ion channels and optogenetics. eLife 7: e42367.
Khan, I. & Arany, P.R. (2016). Photobiomodulation Therapy Promotes Expansion of Epithelial Colony Forming Units. Photomed. Laser Surg. 34: 550-555.
Kucia, M., Reca, R., Campbell, F.R. et al. (2006). A population of very small embryonic-like (VSEL) CXCR4(+)SSEA-1(+)Oct-4+ stem cells identified in adult bone marrow, Leukemia, 20; 5, 857-869.
Kucia, M. Halasa, M. Wysoczynski et al. (2007). Morphological and molecular characterization of novel population of CXCR4+ SSEA-4+ Oct-4+ very small embryonic-like cells purified from human cord blood—preliminary report. Leukemia, 21;2, 297-303.
LaLevesque, J-P., Winkler, I.G., Larsen, S.R. & Rasko, J.E.J. (2007). Mobilization of bone marrow-derived progenitors, in Bone Marrow-Derived Progenitors, 180 Handbook of Experimental Pharmacology, 3-36, Springer, Berlin, Germany.
Lipovski, A., Oron, U., Fedanken, A. & Lubar, R. (2013). Low-level visible light (LLVL) irradiation promotes proliferation of mesenchymal stem cells. Lasers Med. Sci. 28: 1113-1117.

Marais, A., Adams, B., Ringsmuth, A. K., Ferretti, M., Gruber, J. M., Hendrikx, R., Schuld, M., Smith, S. L., Sinayskiy, I., Krüger, T., Petruccione, F., & van Grondelle, R. (2018). The future of quantum biology. Journal of the Royal Society, Interface, 15(148), 20180640. https://doi.org/10.1098/rsif.2018.0640.
Massberg, S. & von Andrian, U.H. (2009). Novel trafficking routes for hematopoietic stem and progenitor cells. Annals of the New York Academy of Sciences, 1176, 87-93.
Park, I-S., Chung, P-S., Ahn, J.C. & Leproux, A. (2017). Human adipose-derived stem cell spheroid treated with photobiomodulation irradiation accelerates tissue regeneration in mouse model of skin flap ischemia. Lasers Med. Sci. 32: 1737-1746.
Quesenberry, P.J., Colvin, G., Dooner, G., Dooner, M., Aliotta, J.M. & Johnson, K. (2007) The stem cell continuum: cell cycle, injury, and phenotype lability, Annals of the New York Academy of Sciences, 1106, 20-29.
Ratajczak, M.Z., Zuba-Surma, E.K., Ratajczak, J., Wysoczynski, & Kucia, M. (2008). Very Small Embryonic Like (VSEL) Stem Cells—Characterization, Developmental Origin and Biological Significance. Exp. Hematol., 36: 742-751.
Sovalat, H., Scrofani, M., Eidenschenk, A. et al. (2011) Identification and isolation from either adult human bone marrow or G-CSF-mobilized peripheral blood of CD34+/CD133+/CXCR4+/ Lin-CD45- cells, featuring morphological, molecular, and phenotypic characteristics of very small embryonic-like (VSEL) stem cells. Exp. Hemat. 39; 4, 495-505.
Sovalat, H., Scrofani, M., Eidenschenk, A. et al. (2016). Human Very Small Embryonic-Like Stem Cells Are Present in Normal Peripheral Blood of Young, Middle-Aged, and Aged Subjects. Stem Cells International 2016: 1-8.
Virant-Klun, I., Skerl, P., Novakovic, S., Vrtacnik-Bokal, E. & Smrkolj, S. (2019). Similar Population of CD133+ and DDX4+ VSEL-Like Stem Cells Sorted from Human Embryonic Stem Cell, Ovarian, and Ovarian Cancer Ascites Cell Cultures: The Real Embryonic Stem Cells?. Cells. 8(7):706. doi:10.3390/cells8070706.
Wang, Y., Huang, Y.Y., Wang, Y. et al (2016). Photobiomodulation (blue and green light) encourages osteoblastic-differentiation of human adipose-derived stem cells: role of intracellular calcium and light-gated ion channels. Sci. Rep. 6: 33719.
Wojakowski, W., Kucia, M., Liu, R. et al. (2011a). Circulating very small embryonic-like stem cells in cardiovascular disease. J. Cardiovasc. Trans. Res. 4 (2):138-144.
Wojakowski, W., Kucia, M., Zuba-Surma, E. et al. (2011b). Very Small Embryonic-Like Stem Cells in Cardiovascular Repair. Pharmacol. Ther. 129(1): 21-28.
Zare, F., Bayat, M., Aliaghaei, A. & Piryaei, A. (2020). Photobiomodulation therapy compensate the impairments of diabetic bone marrow mesenchymal stem cells. Laser Med. Sci. 35: 547-556.
Zuba-Surma, E.K., Kucia, M., Dawn, B., Guo, Y., Ratajczak, M.Z. & Bolli, R. (2008) Bone marrow-derived pluripotent very small embryonic-like stem cells (VSELs) are mobilized after acute myocardial infarction. J Mol Cell Cardiol. 44(5):865-873. doi:10.1016/j.yjmcc.2008.02.279.
Ovokaitys, et al. "Intravenous SONG-modulated laser-activated allogenic cord blood mesenchymal stem cells for the treatment of end-stage heart failure: a preliminary clinical study" CellR4 2021; 9: e3280; DOI: 10.32113/cellr4_202112_3280.
Hollands et al. "Human Very Small Embryonic Like (hVSEL) Stem Cells: Little Miracles" CellR4; 10: e3304; DOI: 10.32113/cellr4_20225_3304.
Brindley et al: A Theoretical Mechanism for the Action of SONG-Modulated Laser Light on Human Very Small Embryonic-Like (hVSEL) Stem Cells in Platelet Rich Plasma (PRP); CellR4; 9: e3201; DOI: 10.32113/cellr4_20216_3201.
International Search Report for PCT/US21/72801, Apr. 18, 2022.
International Search Report for PCT/US24/23137, Aug. 14, 2024.
Kuwasawa et al. "Does intra-articular injection of adipose-derived stem cells imporve cartilage mass? A case report using three-dimensional image analysis software in knee osteoarthritis"; J Med Case Rep., Dec. 21, 2021, vol. 15, No. 1, pp. 1-5.
Zhao et al. "Association of methylenetetrahydrofolate reductase (MTHFR) rs 1801133 (677C>T) gene polymorphism with ischemic

(56) References Cited

OTHER PUBLICATIONS stroke risk in different populations: An updated meta-analysis"; Front Genet., Jan. 4, 2023, vol. 13, No. 1021423, pp. 1-15.
Ong, Wei-Kee et al., The activation of directional stem cell motility by green light-emitting diode irradiation, Dec. 19, 2012, Biomaterials, 34: pp. 1911-1920.
Chen et al: "Homing of endogenous stem/progenitor cells for in situ tissue regeneration: Promises, strategies, and translational perspectives", Biomaterials, Elsevier Science Publishers BV., Barking, GB, vol. 32, No. 12, Dec. 21, 2010 (Dec. 21, 2010), pp. 3189-3209, XP028149163, ISSN: 0142-9612, DOI: 10.1016/J.Biomaterials. 2010.12.032 [retrieved on Dec. 28, 2010].
Taylor et al., "Banking on human embryonic stem cells: estimating the number of donor cell lines needed for HLA matching", Lancet, Dec. 10, 2005; 366: pp. 2019-2025.
International Search Report for PCT/US15/33425, Sep. 29, 2015.
Gatrix, "Supplementing with Light." www.cam-mag.com, CAM Nov. 2012 (2012), enitre document [online] URL=<http://perfect-tp.dyndns-ip.com/DT/perfect/images/mg_cam.pdf>.
International Search Report for PCT/US16/61673, Mar. 2, 2017.
International Search Report for PCT/US15/34236, Sep. 18, 2015.
International Search Report for PCT/US11/24694, Apr. 25, 2011.
International Search Report for PCT/US04/03752, Sep. 7, 2006.
International Search Report for PCT/US08/80098, Feb. 20, 2009.
International Search Report for PCT/US08/80095, Dec. 16, 2008.
Tuby H. et al., "Implantation of low-level laser irradiated mesenchymal stem cells into the infarcted rat heart is associated with reduction in infarct size and enhanced angiogenesis", Photomedicine and Laser Surgery, 2008, vol. 27, No. 2, p. 227-234. DOI: 10.1089/pho.2008. 2272.
Kozlovsky W. J. et al., "Fast amplitude modulation of the blue 429-nm output from a frequency-doubled GaAlAs diode laser", Optics Letters, Feb. 1, 1994, vol. 19, No. 3, pp. 195-197.
Xu X. et al., "Adipose-derived stem cells cooperate with fractional carbon dioxide laser in antagonizing photoaging: a potential role of Wnt and β-catenin signaling", Cell Biosci. May 2, 2014;4:24. doi: 10.1186/2045-3701-4-24.
Ponomarenko G.N. et al., Biophysical Fundamentals of Physiotherapy: Textbook.—Moscow: Public Limited Company "Publishing House Medicine": 2006—176 pages, pp. 148 and 149.
Illarionov V.E., Theory and Practice of Laser Therapy: Textbook. 2nd edition—Moscow: "LIBROCOM" Book House, 2013.—152 pages, pp. 60-61.

\* cited by examiner

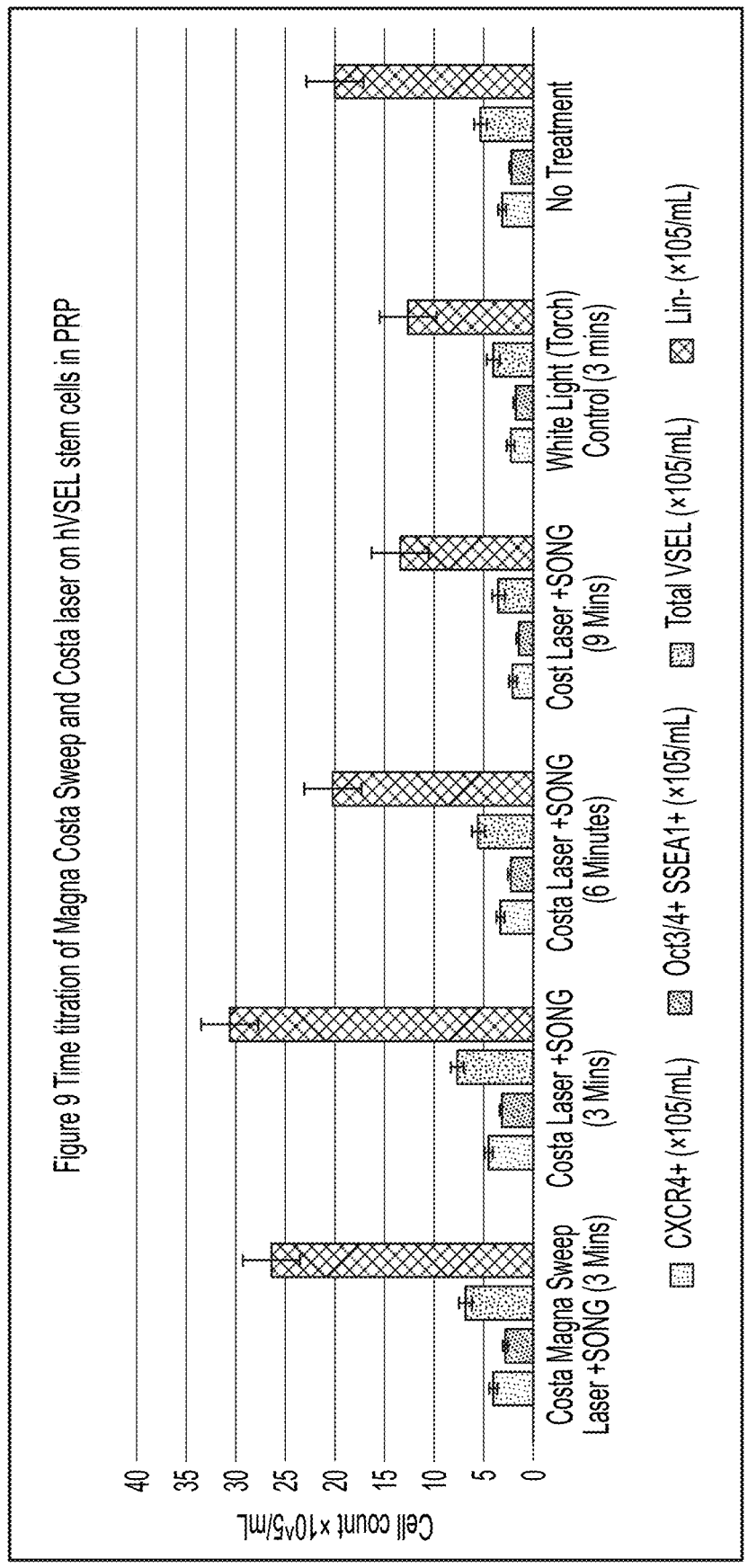

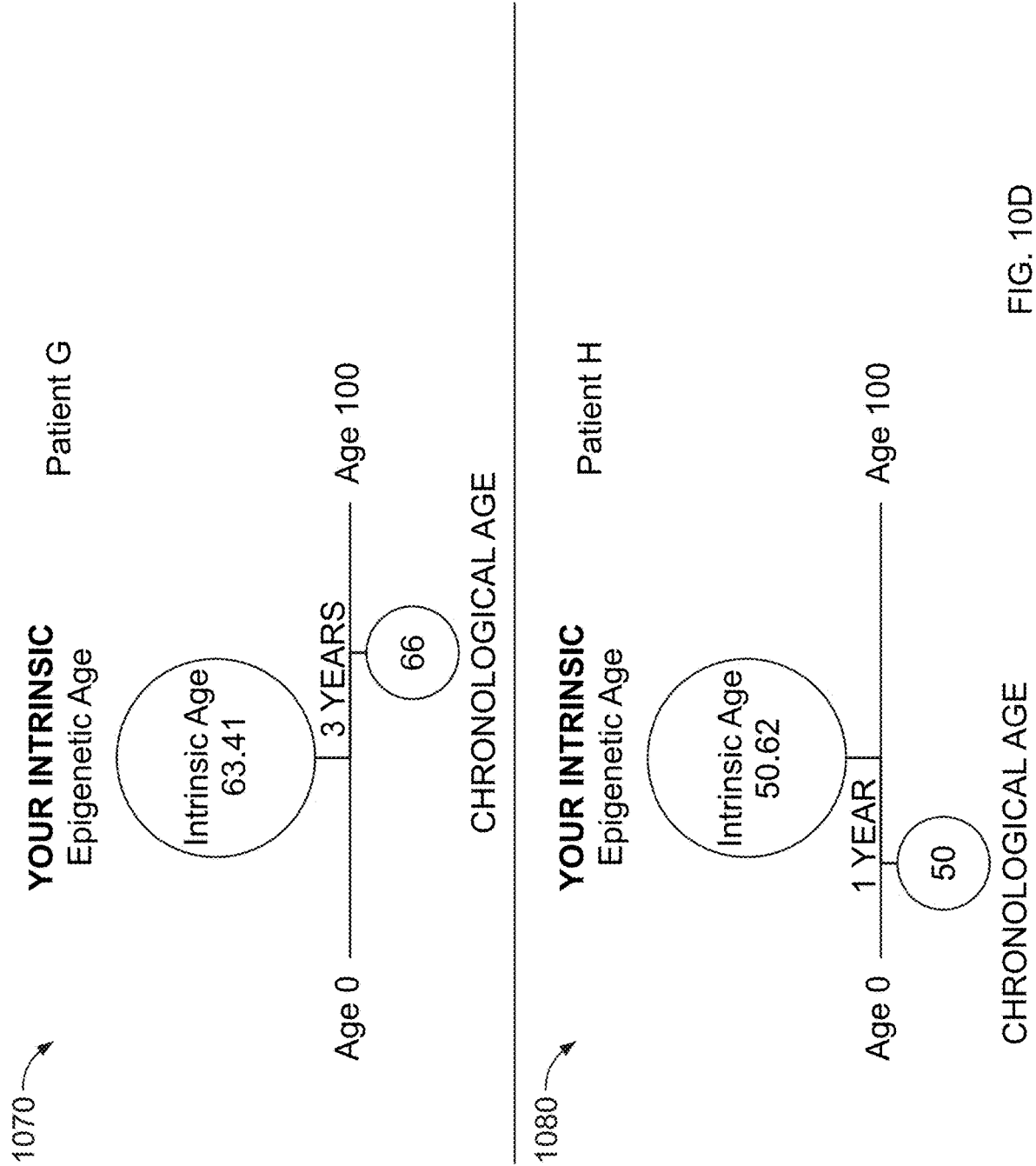

METHODS AND SYSTEMS FOR INCREASED PRODUCTION OF STEM CELLS

CROSS-REFERENCE

The present application relies on the following United States Patent Provisional Applications, for priority, which are herein incorporated by reference in their entirety:

U.S. Patent Provisional Application No. 63/122,831, titled "Methods and Systems for Increased Production of Stem Cells", and filed on Dec. 8, 2020;

U.S. Patent Provisional Application No. 63/122,836, titled "Methods and Systems for Increased Production of Stem Cells", and filed on Dec. 8, 2020; and U.S. Patent Provisional Application No. 63/180,742, titled "Methods and Systems for Increased Production of Stem Cells", and filed on Apr. 28, 2021.

In addition, the present application relates to U.S. Patent Publication Number 20210207121, (U.S. patent application Ser. No. 17/146,849), titled "Methods and Systems for Generation, Use, and Delivery of Activated Stem Cells", filed on Jan. 12, 2021, which is a continuation of U.S. Pat. No. 10,907,144, titled "Methods and Systems for Generation, Use, and Delivery of Activated Stem Cells", issued on Feb. 2, 2021, which, in turn, is a continuation of issued U.S. Pat. No. 10,202,598, of the same title, issued on Feb. 12, 2019, which, in turn, is a continuation-in-part of U.S. Pat. No. 9,999,785, titled "Method and System for Generation and Use of Activated Stem Cells" and issued on Jun. 19, 2018, which, in turn, relies on U.S. Patent Provisional Application No. 62/006,034, filed on May 30, 2014, for priority. The '598 patent further relates to the following United States Provisional Patent Applications, which are also herein incorporated by reference in their entirety: U.S. Provisional Patent Application No. 62/321,781, entitled "Method and System for Generation and Use of Activated Stem Cells", and filed on Apr. 13, 2016; and, U.S. Provisional Patent Application No. 62/254,220, entitled "Method and System for Generation and Use of Activated Stem Cells", and filed on Nov. 12, 2015.

The above-mentioned applications are herein incorporated by reference in their entirety.

FIELD

The present specification discloses methods and systems for the improved production of stem cells and, in particular, the use of modulated laser impulses to increase the proliferation of stem cells to reverse the biological aging process and/or reduce biological age.

BACKGROUND

VSEL (very small embryonic-like) stem cells were first identified in mouse bone marrow and are described as small (1-4 μm) non-haemopoietic cells with a high nuclear to cytoplasm ratio. They express similar surface antigens to pluripotent embryonic stem cells. Human VSEL (hVSEL) stem cells were first identified in umbilical cord blood and have been shown to be CXCR4+, CD34+, CD133+, Oct4+, SSEA4+ and lin−, CD45−. hVSEL stem cells have subsequently been shown to be present in peripheral blood and bone marrow and in leukapheresis samples taken following granulocyte—colony stimulating factor (G-CSF) administration. hVSEL stem cells have since been described in the peripheral blood at a concentration of 800-1300 cells/mL.

hVSEL stem cells are a population of epiblast-derived cells created during embryonic gastrulation. hVSEL stem cells may be important in the long-term production of CD34+ hematopoietic stem cells in the bone marrow and may contribute to repair in experimental myocardial infarction (MI). hVSEL stem cells also persist in peripheral blood throughout life. Accordingly, it may be possible to obtain autologous hVSEL stem cells from any patient at any age, thereby enabling their use in regenerative medicine, simplifying procedures, saving money and reducing adverse reactions associated with allogeneic cells. hVSEL stem cells may also be a viable option to potentially developing pancreatic tissue and human gametes. With correct handling and administration, hVSEL stem cells could play a critical part in translational regenerative medicine in the future.

Laser, and more generally, light technology has been used in the stem cell field. For example, it has been demonstrated that 420 nm and 540 nm laser wavelengths stimulated osteogenic differentiation whereas the other wavelengths did not. Broadband visible light (low-level visible light) has been shown to increase proliferation of bone marrow mesenchymal (MSC) in vitro. The photobiomodulation effects of laser light on dental pulp MSC, human adipose MSC and epithelial colony forming units have also been described.

Flow cytometry is often used to assess laser treated biological samples for cell proliferation. Surface antigens Oct 3/4, SSEA4 and CXCR4 in the lineage negative (Lin−) compartment are assessed using flow cytometry. Of these three markers, it is known that CXCR4 may be blocked from binding by flow cytometry antibodies via its antagonistic ligand, the Endogenous Peptide Inhibitor EPI-X4. This blocking of CXCR4 disrupts or hinders accurate assessment using flow cytometry.

Additionally, organisms have a biological age, which is distinct and separate from the organism's chronological age. The biological age is determined at a cellular level, and may depend on several factors such as lifestyle, environment, and genetics, among other factors. Humans who have a younger biological age as compared to their chronological age are at a lower risk of experiencing age-related diseases. There are well known techniques for measuring biological age. In one example, telomere length is used as an indicator of biological age. In another example, DNA methylation is assessed, which involves a test to determine biological age by measuring intrinsic epigenetic age; thereby relating methylation status to biological age. It has been determined that DNA methylation age is close to zero for embryonic and induced pluripotent stem cells.

What is needed, therefore, is a method of increasing the amount of stem cells per volume of platelet rich plasma (PRP) fluid. Specifically, what is needed is a method of using modulated laser photobiomodulation to increase the proliferation of peripheral blood hVSEL stem cells. What is also needed is a method to unblock CXCR4 thus making it readily available for binding to flow cytometry antibodies. Additionally, is desirable to have a method for slowing down or reversing the biological clock so that a biological age is less than a chronological age of an organism.

SUMMARY

The following embodiments and aspects thereof are described and illustrated in conjunction with systems, tools and methods, which are meant to be exemplary and illustrative, not limiting in scope. The present specification discloses numerous embodiments.

In some embodiments, the present specification is directed towards a method of reducing biological age of a patient comprising: proliferating stem cells of the patient, wherein the proliferation comprises preparing platelet rich plasma containing stem cells and treating the platelet rich plasma containing stem cells with modulated pulses of laser light having a predefined wavelength and for a predefined period of time; and, administering the treated platelet rich plasma to the patient.

Optionally, the platelet rich plasma is prepared by: adding the patient's blood into a plurality of tubes; centrifuging the plurality of tubes at a predefined g force for a predefined period of time to produce the platelet rich plasma; and aliquoting the produced platelet rich plasma into a sterile tube.

Optionally, the centrifuging the plurality of tubes further comprises shaking the plurality of tubes after centrifuging.

Optionally, the method further comprises shaking the sterile tube after aliquoting.

Optionally, the plurality of tubes ranges from 3 tubes to 12 tubes, and any increment therein.

Optionally, the method further comprises shaking the platelet rich plasma after treating with modulated pulses of laser light.

Optionally, the treatment of the platelet rich plasma is carried out in minimum background white light conditions.

Optionally, the predefined wavelength ranges from 300 nm to 1000 nm. Still optionally, the predefined wavelength is 670 nm.

Optionally, the platelet rich plasma is prepared using normal human blood.

Optionally, the predefined period of time ranges from 1 minute to 5 minutes.

Optionally, the treated platelet rich plasma has an amount of stem cells ranging from $0.5 \times 10^6$/mL to $2.0 \times 10^6$/mL when analyzed immediately after the predefined period of time. Optionally, the treated platelet rich plasma has an amount of stem cells ranging from $0.5 \times 10^6$ per mL to $2.0 \times 10^6$ per mL when analyzed immediately after the predefined period of time.

Optionally, the patient experiences a decrease in biological age in a range of 1 year to 4 years based on a first administration of the treated platelet rich plasma. Still optionally, the patient experiences a decrease in biological age in a range of 4 years to 9 years based on a second administration of the treated platelet rich plasma. Optionally, the second administration of the treated platelet rich plasma occurs 1 week to 6 months after the first administration.

In some embodiments, the present specification discloses a method of reducing biological age of a patient comprising: proliferating stem cells of the patient, comprising: adding normal human blood into a plurality of tubes; centrifuging the plurality of tubes at a predefined g force for 10 minutes to produce platelet rich plasma; shaking the plurality of tubes; aliquoting the produced platelet rich plasma into a sterile tube; shaking the platelet rich plasma in the sterile tube; treating the platelet rich plasma with modulated pulses of laser light having a predefined wavelength and for a predefined period of time; and shaking the treated platelet rich plasma; and, administering the treated platelet rich plasma to the patient.

Optionally, the plurality of tubes ranges from 3 tubes to 12 tubes, and any increment therein.

Optionally, the treatment of the platelet rich plasma is carried out in minimum background white light conditions.

Optionally, the predefined wavelength ranges from 300 nm to 1000 nm. Still optionally, the predefined wavelength is 670 nm.

Optionally, the predefined period of time ranges from 1 minute to 5 minutes.

Optionally, the treated platelet rich plasma has an amount of stem cells ranging from $0.5 \times 10^6$/mL to $2.0 \times 10^6$/mL when analyzed immediately after the predefined period of time. Optionally, the treated platelet rich plasma exhibits a 2.5 fold increase in stem cells compared to a mean of first and second control samples, wherein the first control sample includes the platelet rich plasma treated with white torch light for the predefined period of time, and wherein the second control sample includes the platelet rich plasma without any light treatment.

Optionally, the modulation cancels a central wavelength band of the laser light such that the remaining upper and lower wavelength bands create a beat frequency pattern of sparse nodes.

Optionally, the patient experiences a decrease in biological age in a range of 1 year to 4 years based on a first administration of the treated platelet rich plasma. Still optionally, the patient experiences a decrease in biological age in a range of 4 years to 9 years based on a second administration of the treated platelet rich plasma. Optionally, the second administration of the treated platelet rich plasma occurs 1 week to 6 months after the first administration.

In some embodiments, the present specification discloses a method of producing a composition that, when administered to a patient, reduces a biological age of a patient comprising: proliferating stem cells of the patient comprising: preparing platelet rich plasma containing stem cells; and treating the platelet rich plasma with modulated pulses of laser light having a predefined wavelength and for a predefined period of time.

Optionally, the platelet rich plasma is prepared by: adding the patient's blood into a plurality of tubes; centrifuging the plurality of tubes at a predefined g force for a predefined period of time to produce the platelet rich plasma; and aliquoting the produced platelet rich plasma into a sterile tube.

Optionally, the centrifuging the plurality of tubes further comprises shaking the plurality of tubes after centrifuging.

Optionally, the method further comprises shaking the sterile tube after aliquoting.

Optionally, the plurality of tubes ranges from 3 tubes to 12 tubes, and any increment therein.

Optionally, the method further comprises shaking the platelet rich plasma after treating with modulated pulses of laser light.

Optionally, the treatment of the platelet rich plasma is carried out in minimum background white light conditions.

Optionally, the predefined wavelength ranges from 300 nm to 1000 nm. Still optionally, the predefined wavelength is 670 nm.

Optionally, the platelet rich plasma is prepared using normal human blood.

Optionally, the predefined period of time ranges from 1 minute to 5 minutes.

Optionally, the treated platelet rich plasma has an amount of stem cells ranging from $0.5 \times 10^6$/mL to $2.0 \times 10^6$/mL when analyzed immediately after the predefined period of time.

In some embodiments, the present specification describes a method of producing a composition that, when administered to a patient, reduces a biological age of a patient comprising: proliferating stem cells of the patient, comprising: adding normal human blood into a plurality of tubes;

centrifuging the plurality of tubes at a predefined g force for 10 minutes to produce platelet rich plasma; shaking the plurality of tubes; aliquoting the produced platelet rich plasma into a sterile tube; shaking the platelet rich plasma in the sterile tube; treating the platelet rich plasma with modulated pulses of laser light having a predefined wavelength and for a predefined period of time; and shaking the treated platelet rich plasma.

Optionally, the plurality of tubes ranges from 3 tubes to 12 tubes, and any increment therein.

Optionally, the treatment of the platelet rich plasma is carried out in minimum background white light conditions.

Optionally, the predefined wavelength ranges from 300 nm to 1000 nm. Optionally, the predefined wavelength is 670 nm.

Optionally, the predefined period of time ranges from 1 minute to 5 minutes.

Optionally, the treated platelet rich plasma has an amount of stem cells ranging from $0.5 \times 10^6$/mL to $2.0 \times 10^6$/mL when analyzed immediately after the predefined period of time.

Optionally, the treated platelet rich plasma exhibits a 2.5 fold increase in stem cells compared to a mean of first and second control samples, wherein the first control sample includes the platelet rich plasma treated with white torch light for the predefined period of time, and wherein the second control sample includes the platelet rich plasma without any light treatment.

Optionally, the modulation cancels a central wavelength band of the laser light such that the remaining upper and lower wavelength bands create a beat frequency pattern of sparse nodes.

In some embodiments, the present specification discloses a method of reducing biological age of a patient comprising: proliferating stem cells of the patient comprising: preparing platelet rich plasma containing stem cells; and treating the platelet rich plasma with modulated pulses of laser light having a predefined wavelength and for a predefined period of time.

Optionally, the platelet rich plasma is prepared by: adding the patient's blood into six tubes; centrifuging the six tubes at a predefined g force for a predefined period of time to produce the platelet rich plasma; and aliquoting the produced platelet rich plasma into a sterile tube. Optionally, centrifuging the six tubes further comprises shaking the six tubes after centrifuging. Optionally, the method further comprises shaking the sterile tube after aliquoting.

Optionally, the method further comprises shaking the platelet rich plasma after treating with modulated pulses of laser light.

Optionally, said treatment of the platelet rich plasma is carried out in minimum background white light conditions.

Optionally, the predefined wavelength ranges from 300 nm to 1000 nm.

Optionally, the predefined wavelength is 670 nm.

Optionally, the platelet rich plasma is prepared using normal human peripheral blood.

Optionally, the predefined period of time is 3 minutes.

Optionally, said treated platelet rich plasma has $1.256 \times 10^6$/mL of stem cells when analyzed immediately after the predefined period of time.

In some embodiments, the present specification also discloses a method of reducing biological age of a patient comprising: proliferating stem cells of the patient, comprising: adding normal human peripheral blood into six tubes; centrifuging the six tubes at a predefined g force for 10 minutes to produce platelet rich plasma; shaking the six tubes; aliquoting the produced platelet rich plasma into a sterile tube; shaking the platelet rich plasma in the sterile tube; treating the platelet rich plasma with modulated pulses of laser light having a predefined wavelength and for a predefined period of time; and shaking the treated platelet rich plasma.

Optionally, said treatment of the platelet rich plasma is carried out in minimum background white light conditions.

Optionally, the predefined wavelength ranges from 300 nm to 1000 nm.

Optionally, the predefined wavelength is 670 nm.

Optionally, the predefined period of time is 3 minutes.

Optionally, said treated platelet rich plasma has $1.256 \times 10^6$/mL of stem cells when analyzed immediately after the predefined period of time.

Optionally, said treated platelet rich plasma exhibits a 2.5 times increase in stem cells compared to a mean of first and second control samples, wherein the first control sample includes the platelet rich plasma treated with white torch light for the predefined period of time, and wherein the second control sample includes the platelet rich plasma without any light treatment.

Optionally, said modulation cancels a central wavelength band of the laser light such that the remaining upper and lower wavelength bands create a beat frequency pattern of sparse nodes.

In some embodiments, the present specification is directed toward a method of proliferating stem cells comprising: preparing platelet rich plasma containing stem cells; and treating the platelet rich plasma with modulated pulses of laser light having a predefined wavelength and for a predefined period of time.

Optionally, the platelet rich plasma is prepared by: adding donated normal human peripheral blood into three tubes; centrifuging the three tubes at a predefined g force for a predefined period of time to produce the platelet rich plasma; and aliquoting the produced platelet rich plasma into a single sterile tube.

Optionally, said treatment of the platelet rich plasma is carried out in minimum background white light conditions.

Optionally, the predefined wavelength ranges from 300 nm to 1000 nm.

Optionally, the predefined wavelength is 670 nm.

Optionally, the platelet rich plasma is prepared using donated normal human peripheral blood.

Optionally, the predefined period of time is 3 minutes.

Optionally, said treated platelet rich plasma has $1.256 \times 10^6$/mL of stem cells when analyzed immediately after the predefined period of time.

In some embodiments, the present specification discloses a method of proliferating stem cells comprising: adding donated normal human peripheral blood into three tubes; centrifuging the three tubes at a predefined g force for 10 minutes to produce platelet rich plasma; aliquoting the produced platelet rich plasma into a single sterile tube; and treating the platelet rich plasma with modulated pulses of laser light having a predefined wavelength and for a predefined period of time.

Optionally, said treatment of the platelet rich plasma is carried out in minimum background white light conditions.

Optionally, the predefined wavelength ranges from 300 nm to 1000 nm.

Optionally, the predefined wavelength is 670 nm.

Optionally, the predefined period of time ranges from 1 to 6 minutes. Optionally, the predefined period of time ranges from 1 to 3 minutes. Optionally, the predefined period of time is 3 minutes. Optionally, the predefined period of time is dependent upon the volume of platelet rich plasma.

Optionally, said treated platelet rich plasma has 1.256× $10^6$/mL of stem cells when analyzed immediately after the predefined period of time.

Optionally, said treated platelet rich plasma exhibits a 2.5 times increase in stem cells compared to a mean of first and second control samples, wherein the first control sample includes the platelet rich plasma treated with white torch light for the predefined period of time, and wherein the second control sample includes the platelet rich plasma without any light treatment.

Optionally, said modulation cancels a central wavelength band of the laser light such that the remaining upper and lower wavelength bands create a beat frequency pattern of sparse nodes.

The aforementioned and other embodiments of the present shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 9 is a graph illustrating data pertaining to time titration of SONG modulated Magna Costa and Costa Laser on hVSEL Stem Cells in PRP;

FIG. 10D illustrates an IEA of yet another two patients; and

DETAILED DESCRIPTION

Figure 1:
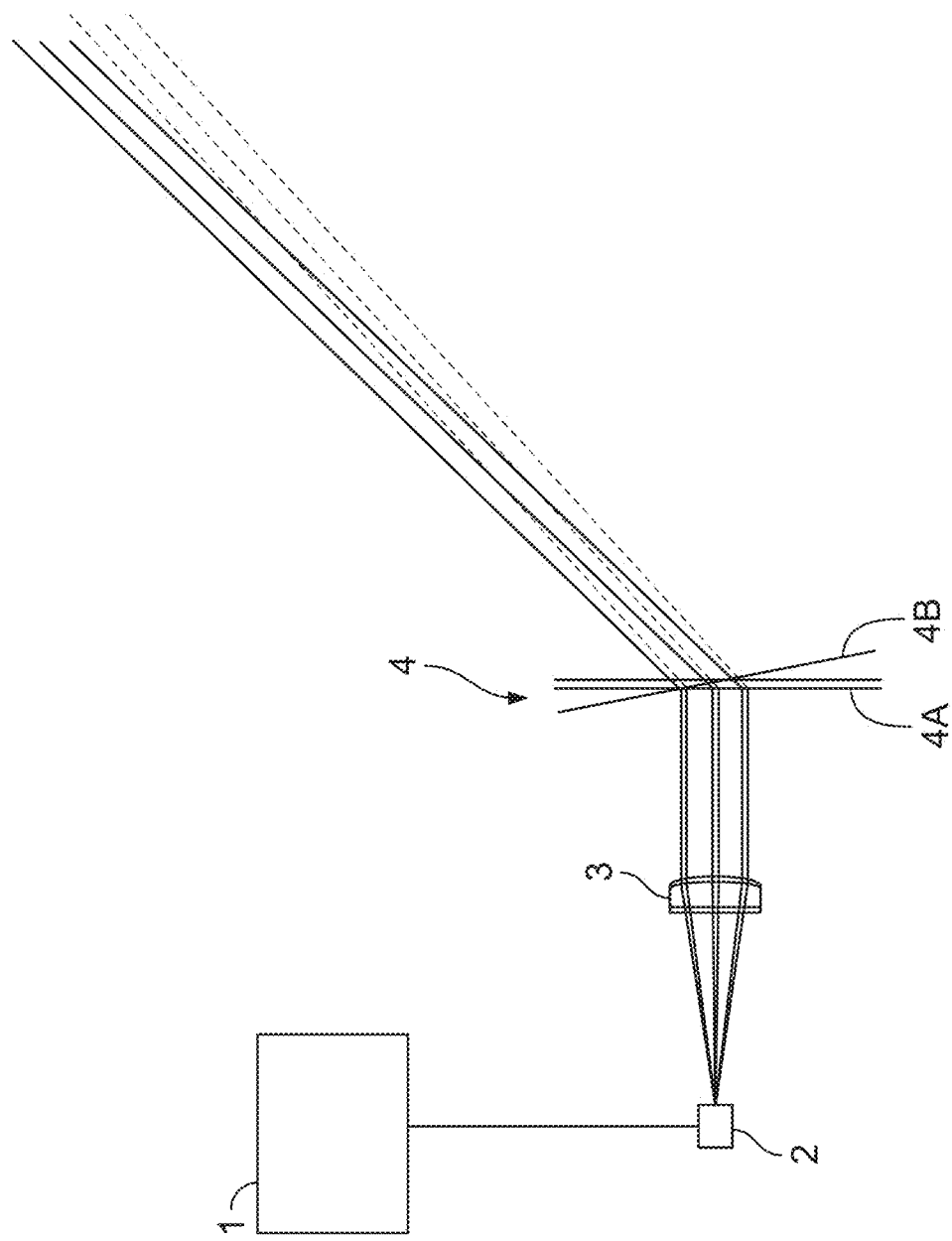
FIG. 1 illustrates a Strachan-Ovokaitys Node Generator (SONG) device as disclosed in U.S. Pat. No. 6,811,564, which is incorporated herein by reference in its entirety.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

In embodiments, intrinsic epigenetic age (IEA) refers to a true biological age at the DNA level. In embodiments, extrinsic epigenetic age (EEA) refers to an organism's immune function status in addition to other factors that are more responsive to external factors such as diet, lifestyle and supplement use.

In embodiments, "normal human blood" is defined as blood in a chemical and physical state as when immediately withdrawn from a human and without any further processing, whether mechanical and/or chemical, also referred to as non-processed human blood. As used in this specification, peripheral blood is the fluid that travels through the heart, arteries, capillaries, and veins. It serves to transport oxygen and other nutrients to the body's cells and tissues and to remove carbon dioxide and other waste products from the body. Peripheral blood also plays an essential role in the immune system, delivery of hormones, and temperature regulation.

Platelet-rich plasma (PRP) may be defined, as used in this specification, as plasma that has a heightened amount of platelets due to some form of mechanical and/or chemical processing relative to plasma that has not undergone that processing.

SONG Device

In various embodiments, for increased production or proliferation, the stem cells are treated with a laser process that exposes the stem cells to a predefined laser wavelength at a predefined amplitude modulation that is passed through a beam expander, typically on the order of 5× to 10×, (though greater or lesser could be used) and in conjunction with a device for optical phase conjugation such as a Strachan-Ovokaitys Node Generator or SONG device, which is disclosed in U.S. Pat. No. 6,811,564 and incorporated herein by reference.

FIG. 1 illustrates a SONG device as disclosed in U.S. Pat. No. 6,811,564. Referring to FIG. 1, the SONG device comprises a laser diode 2 which is controlled by an amplitude modulator 1. The laser diode 2 is selected to have a substantially linear relationship between current and wavelength with minimum mode hopping. The amplitude modulator 1 modulates the current to the laser diode 2 which, in turn, results in a very small wavelength modulation of the laser, for purposes discussed below.

Figure 2:
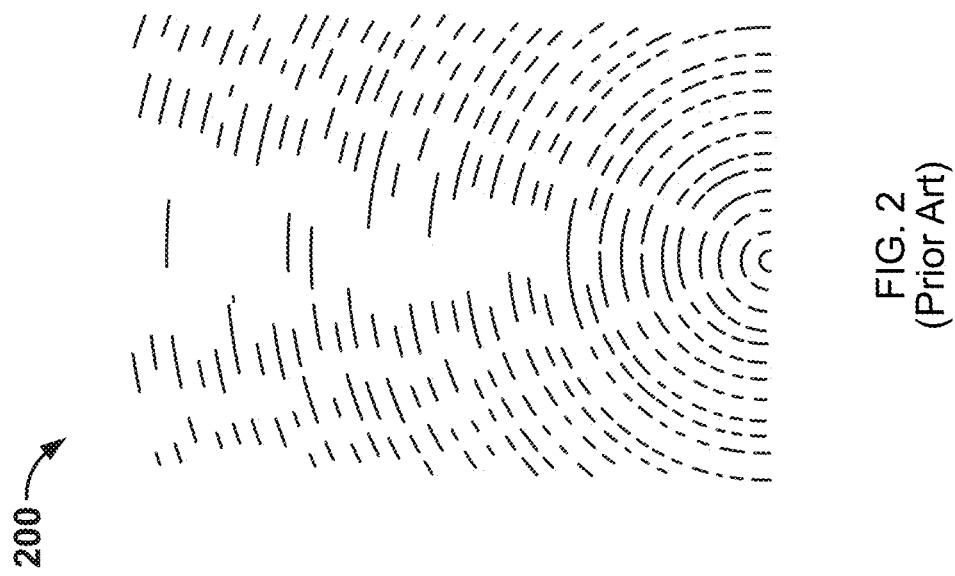
FIG. 2 shows a sparse constructive interference effect from a 1 percent bandwidth cancellation plate having a 5 mm aperture.

The output of the laser diode 2 is collimated by a lens 3 and passed to an optical element 4. The optical element 4 consists of a first diffraction grating, a refractive element, and a second diffraction grating such that the beam is substantially cancelled. This allows the cancellation to occur over a small percentage of the wavelength variance of the laser source, rather than at a single critical wavelength. Wavelengths beyond the acceptance bandwidth of the cancelling optic 4 above and below the center frequency pass without being cancelled. This means that a complex Fresnel/Fraunhoffer zone is generated, defined by the beat frequency of the high and low frequencies as a function of the aperture. Consequently, relatively sparse zones of constructive interference occur between the high and low frequency passes of the cancellation element in selected directions from the aperture, as shown in FIG. 2. FIG. 2 shows the sparse constructive interference effect from a 1 percent bandwidth cancellation plate of 5 mm aperture. Black represents constructive nodes.

As seen in FIG. 1, the optical element 4 can be adjusted angularly between positions 4A and 4B. This varies the ratio of constructive to destructive interference. Additionally, in embodiments, the system of FIG. 1 may include mechanisms for aligning the resultant beam emerging from optical element 4, in a straight line with the collimated beam emerging from collimator 3.

In effect, the continuous beam is transformed into a string of extremely short duration pulses typically on the order of a duration in subfemtoseconds. The small wavelength modulation of the laser diode 2 causes the constructive and destructive nodes to move rapidly through the volume of the Fresnel zone of the collimator lens aperture. This has the effect of stimulating very short (subpicosecond) pulse behavior at any point in the Fresnel zone through which the nodes pass at a pulse repetition frequency defined by the amplitude modulator frequency.

The wavelength of the cancellation and constructive interference zones for a theoretical single path would be the difference between the two frequencies. If the bandwidth of the cancelling element is narrow, this difference is very small and the effective wavelength of the cancelled/non-cancelled cycle would be very long, on the order of picoseconds. Therefore, the system would behave substantially similarly to a system with no cancellation because it requires an aperture much larger than the primary light wavelength to generate a useful Fresnel/Fraunhoffer zone. Such an aperture would greatly multiply the available Feynman diagram paths eliminating any useful effect, even if it were possible to generate a sufficiently coherent source of such an aperture.

If the beat frequency can be made high enough, the wavelength of the cancelled to non-cancelled cycle can be a fraction of a practical aperture. This will make this wavelength sufficiently small to limit the Feynman paths to within a cycle or two in free space allowing the Fresnel/Fraunhoffer effect to be apparent. Since the center frequency and spectrum spread of a laser diode is modulated by adjusting the current and/or temperature of the junction, the pattern of the Fresnel/Fraunhoffer zones is varied substantially by very small variations in the wavelength of one or both pass frequencies. Such modulation is produced in the apparatus of FIG. 1 by the amplitude modulator 2.

A conventional coherent or incoherent beam would have high probability paths in the Feynman diagram. These paths would overlap at very low frequencies (kHz) and be of little practical use in the stimulation of molecular resonance. It should be noted however that the phenomena described above is used as a means to multiply the modulation frequency, up to the point where the beam effectively becomes continuous. Thus, by properly selecting the aperture, the region of the beam selected for transmission through the medium, and the modulation frequency, it is possible to cause the constructive nodes to pass across any given point in the beam at frequencies many times higher than the modulation frequency. In ideal conditions, the duration of exposure to a constructive node of any point would be for a period equivalent to a quarter of the duration of a wavelength of the molecular frequency repeated once per cycle.

If the wavelength of the laser is chosen to be one easily absorbed by the atomic structures it is desired to induce to resonance, then the beam will efficiently deliver the desired modulation frequency to the desired molecules. Cell adhesion molecules and human integrins such as alpha 4 and beta 1 are ideally suited for excitation to chemical activity by this method.

The sources of cells for the procedure described herein may be autologous or exogenous. Autologous stem cells refer to cells which are derived from the same person who is to be treated with such cells. These cells will be a genetic match obviating risks of rejection of cells. In current methods, autologous stem cells are either derived or concentrated from peripheral blood, bone marrow or fat, yet other tissues could be a source of autologous stem cells as virtually every tissue of the body has its own distinct stem cell reservoir.

A preferred exogenous source of stem cells is umbilical cord blood. Stem cells from cord blood are very robust with long telomeres (a genetic aging clock level of newborn level) and a strong capacity for tissue repair. Functionally, rejection syndromes of the cells and graft versus host disease (GVHD) have not been an issue with this source of cells in the context of an intact immune system. Matched bone marrow could also be a source of cells, though a high degree of matching would be required to avoid rejection and GVHD. In practice, for regeneration as opposed to anti-leukemic medical regimes, cord blood stem cells have been used safely.

Preparation of Platelet Rich Plasma (PRP) Containing hVSEL Stem Cells

Figure 3:
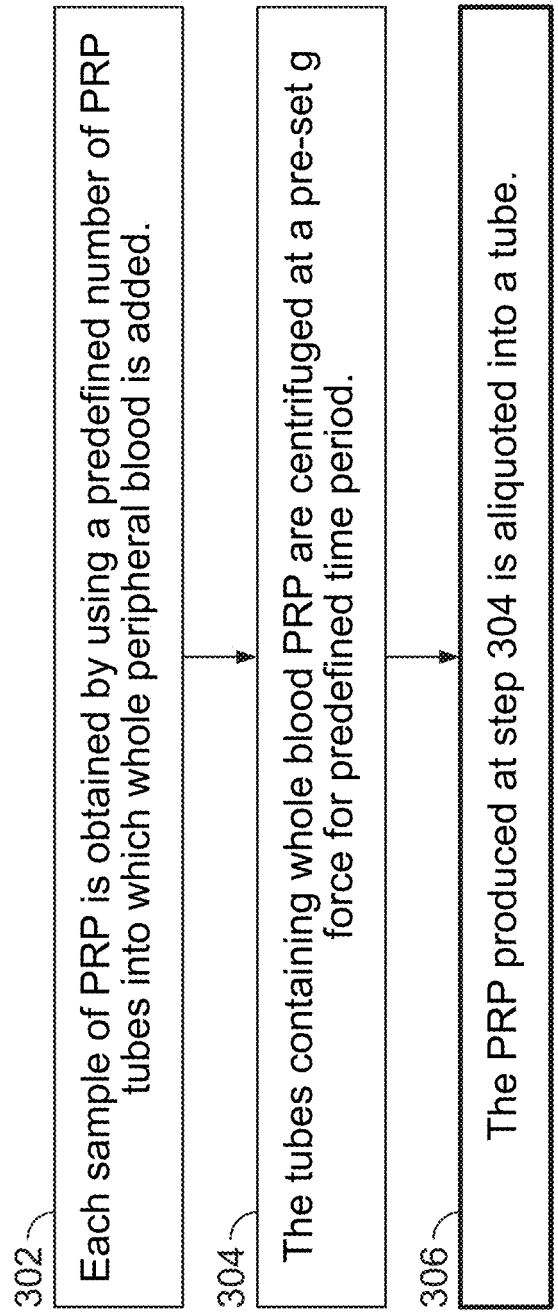
FIG. 3 is a flowchart illustrating steps of a method of preparing PRP containing hVSEL stem cells, in accordance with some embodiments of the present specification.

FIG. 3 is a flowchart illustrating a method of preparing PRP that contains hVSEL stem cells, in accordance with some embodiments of the present specification. Anti-coagulated (sodium citrate) donated normal human peripheral blood (450 mL) was acquired and kept at 4° C. before use. The blood was allowed to warm to room temperature before processing for PRP.

At step 302, each sample of PRP is obtained by using three PRP tubes into which 11 mL of whole peripheral blood (normal human blood) is added/aliquoted. At step 304, the tubes containing whole blood PRP are centrifuged at a pre-set g force for 10 minutes. Consequently, each of the three PRP tubes containing 11 mL of whole blood produces approximately 6 mL (a total of approximately 18 mL) of PRP.

At step 306, the PRP produced at step 304 is aliquoted, using aseptic technique in a Class II flow hood, into a single sterile tube for further manipulation and analysis. Each 18 mL PRP preparation is created in triplicate for each manipulation and assessment process.

Processing, Modulation, Manipulation and Assessment of Human PRP Containing hVSEL Stem Cells In accordance with aspects of the present specification, PRP containing hVSEL stem cells are manipulated or modified using pulses of laser light having a wavelength in a range of 300 nm to 1000 nm, and, in an embodiment, approximately 670 nm. In some embodiments, PRP containing hVSEL stem cells is manipulated or modified using the following two lasers:

Costa Laser: The Costa Laser employed is, in an embodiment, a 670 nm, 5 mW SONG modulated laser. In embodiments, the level of optical phase conjugation (OPC) was varied for experimental purposes. In embodiments, a level of optical phase conjugation ranges from 1% to 99%. In an embodiment, the SONG modulated laser was set at 60% optical phase conjugation (OPC) for a resultant beam power of 1 mW.

Magna Costa Laser: The Magna Costa laser employed is, in an embodiment, a 670 nm, 5.7 mW SONG modulated laser. In embodiments, the level of optical phase conjugation (OPC) was varied for experimental purposes. In embodiments, a level of optical phase conjugation ranges from 1% to 99%. In an embodiment, the SONG modulated laser was set at 60% OPC for a resultant beam power of 1.3 mW. The Magna Costa laser has adjustable wave forms to enable alternative wave forms to be introduced as a control.

In embodiments, SONG modulation of the laser cancels the central wavelength band of the laser output as a result of non-fringing destructive interference. The remaining upper and lower wavelength bands create a beat frequency pattern of sparse nodes of constructive interference which represents the physical visible light that remains. Modulation of this complex wave form pattern results in a rapid traverse of these nodes that can reach pulse repetition frequencies every femtosecond or less. The destructive interference and sparseness of the nodes reduces the flare at the surface of the tissue interface. This decreases both the reflectiveness of photons which have entered a zone that has just experienced photon absorption as well as a scattering effect. The depth of penetration of sparse nodes may be 10-20 times that of ordinary photons at the surface of an interface such as human skin.

Culture and Harvesting of Laser-Treated and Control (No Laser or White Light) hVSEL in PRP In some embodiments, to assess the biological stability of the effect of laser exposure or manipulation, the PRP is cultured in equal volumes of RPMI 1640 media supplemented with 200 mM L-Glutamine, penicillin, and streptomycin and 10% heat inactivated fetal calf serum.

All PRP cultures are carried out using T25 vented flasks in a humidified incubator set at 37° C. and 5% $CO_2$ in air. Adherent cells are harvested when needed in an initial wash with Ca2+/Mg2+ free Dulbecco's PBS and treatment with Trypsin EDTA for 5 minutes at 37° C.

The Numbers and Distribution of hVSEL Stem Cells in Untreated PRP

In an embodiment, to assess the distribution and numbers of hVSEL stem cells in untreated PRP tubes of PRP are separated into discrete sample tubes following centrifugation (see the flowchart of FIG. 3) by taking 2 mL of the 'top' portion of PRP; 2 mL of the 'middle' portion of PRP; 2 mL of the 'bottom' portion PRP—as close to the red cell interface as possible; 2 mL of the top of the red cell section; and 2 mL at the bottom of the red cell section for a total of five tubes per PRP sample. Each sample is assessed for hVSEL stem cell numbers using the flow cytometry protocol mentioned earlier in this specification. Assessment of each sample showed that cell viability remained at >90%.

Figure 4:
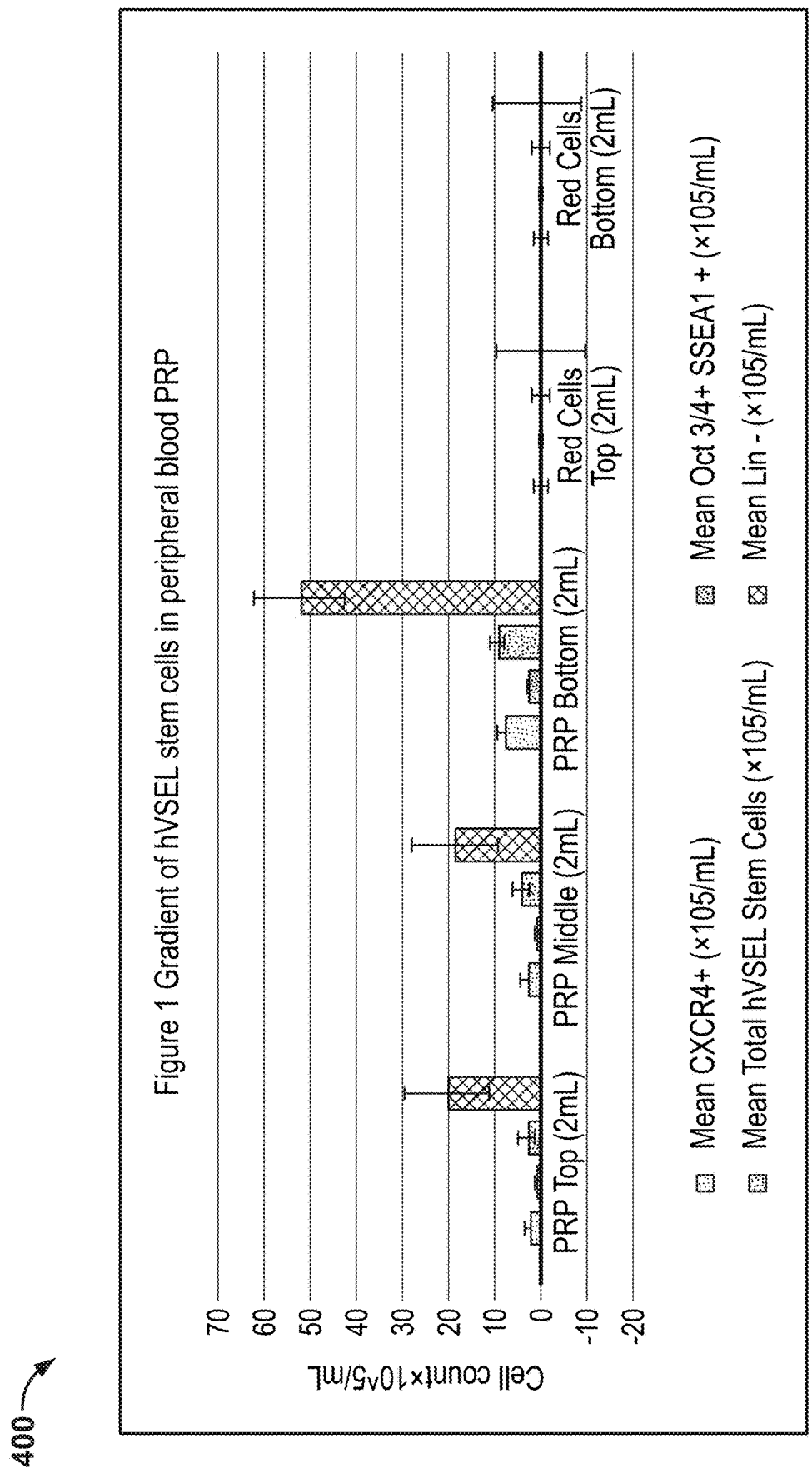
FIG. 4 is a graph showing data on the numbers and distribution of hVSEL stem cells in untreated PRP.

FIG. 4 is a graph 400 illustrating data on the number and distribution of hVSEL stem cells in untreated PRP for each of the portions obtained in the method described with respect to FIG. 3. The top 2 mL of the PRP is found to have a mean hVSEL stem cell count of $3.1 \times 10^5$/mL and the mean Lin– cell count was $20.0 \times 10^5$/mL. The middle 2 mL of the PRP is found to have a mean hVSEL stem cell count of $4.27 \times 10^5$/mL and the mean Lin– cell count is $18.5 \times 10^5$/mL. The bottom 2 mL of the PRP is found to have a mean hVSEL stem cell count of $9.29 \times 10^5$/mL and the mean Lin– cell count is $52.2 \times 10^5$/mL. The total mean number of hVSEL stem cells found in PRP is $1.66 \times 10^6$/mL. The total mean number of Lin– cells found in the PRP is $9.01 \times 10^6$/mL. The total number of hVSEL stem cells in the red cell top section is $4.0 \times 10^2$/mL and the mean Lin–cell count is $1.65 \times 10^4$/mL. The total number of hVSEL stem cells in the red cell bottom section is $6.0 \times 10^2$/mL and the mean Lin– cell count is $5.1 \times 10^4$/mL.

In this embodiment, it is shown that there is a mean of $1.6 \times 10^6$/mL hVSEL stem cells in PRP obtained from donated human blood. It is also possible to provide another mean estimate of the total hVSEL stem cells/mL in PRP by taking the mean of the no treatment values for PRP across all of the different extractions. This produces a mean value of $3.92 \times 10^6$/mL. The range of observed hVSEL stem cells in PRP normal peripheral blood (normal human blood) in the present gradient study is $0.746-16 \times 10^5$/mL.

The PRP is found to have a gradient of hVSEL stem cells increasing from the top meniscus of the PRP all the way down to the PRP/red cell interface where the highest number of hVSEL stem cells is found, indicating that the entire volume of PRP should be used for optimal results in some embodiments. Accordingly, multiple volumes of PRP are pooled for clinical applications. In embodiments, some applications may require a higher hVSEL concentration per volume of PRP. For example, in some applications, such as hair and cosmetic applications, which are localized, it is desirable to have a higher hVSEL concentration. In these cases, the bottom third portion where the highest number of hVSEL cells is present may be used for a more concentrated effect. In other applications, for example, in systemic treatment that may be administered intravenously, it may be desirable to pool the entire volume.

Figure 5:
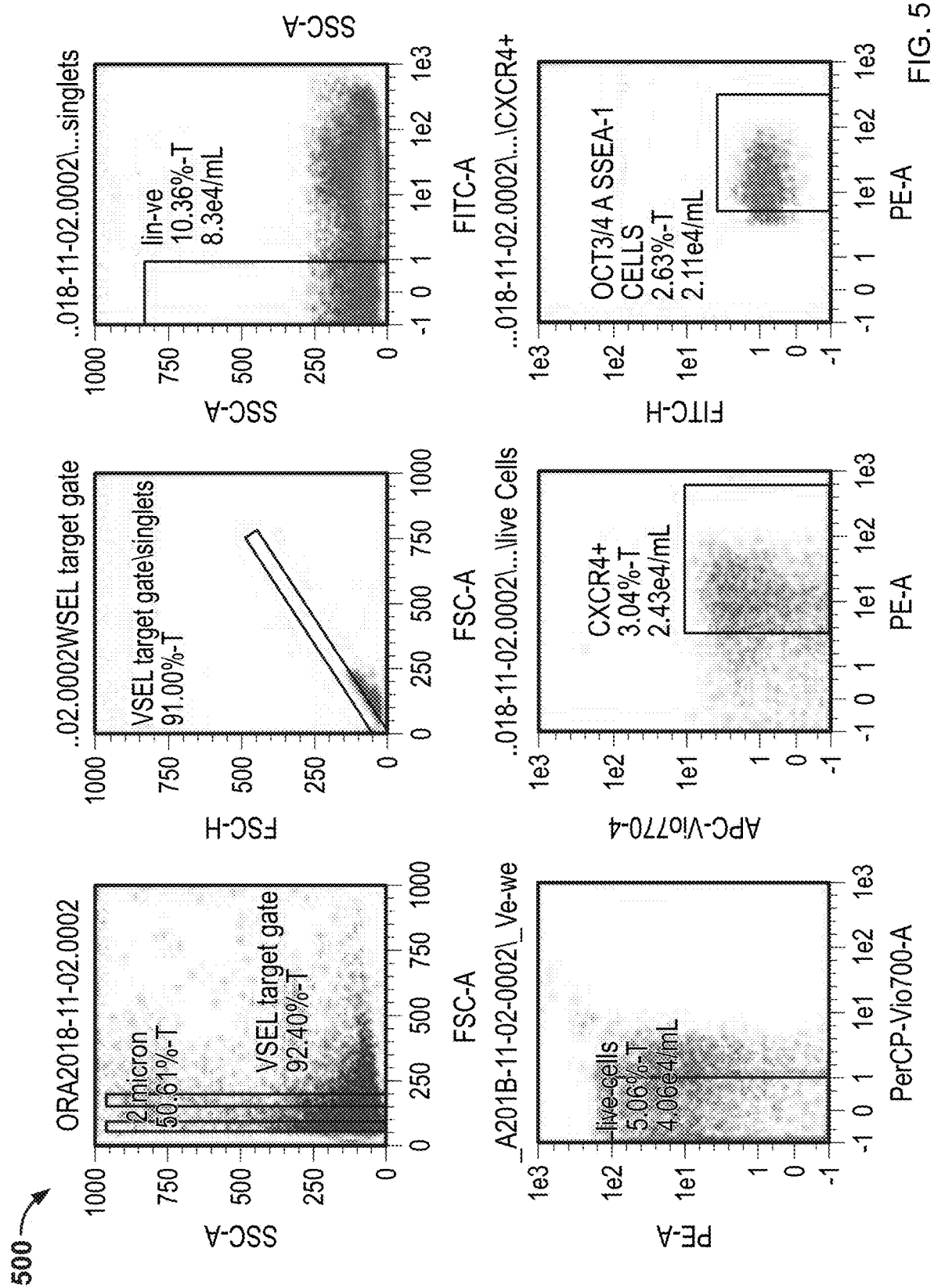
FIG. 5 illustrates a result of a typical flow cytometer for PRP with no laser treatment.

There are very few (approximately $1 \times 10^3$/mL) hVSEL stem cells in the red cell section of the PRP tube. These data show that the PRP based isolation of hVSEL stem cells works very efficiently when using the systems and methods of the present specification. FIG. 5 shows results 500 of a typical flow cytometer for PRP with no laser treatment.

Laser Treatment (Using Costa Laser) of PRP and Resulting hVSEL Stem Cell Proliferation on Day 0 and Day 1 of Culture In an embodiment, to assess the effect of a Costa laser with SONG modulation on hVSEL stem cell numbers in PRP, PRP is prepared as described earlier with reference to FIG. 3, in triplicate. A first batch is exposed to Costa laser +SONG (set at 60% OPC)) light for 3 minutes, a second batch is exposed to white torch light for 3 minutes, and a third batch received no treatment (control). Following flow cytometer analysis, the three PRP samples are cultured and then harvested for flow cytometry analysis on day 1. The purpose of this embodiment is to assess the initial effects of the laser on hVSEL stem proliferation and to see if these changes were stable after 24 hours in culture in vitro. Others have described gene upregulation in human dermal cells following laser exposure which resulted in increased paracrine secretions.

Figure 6:
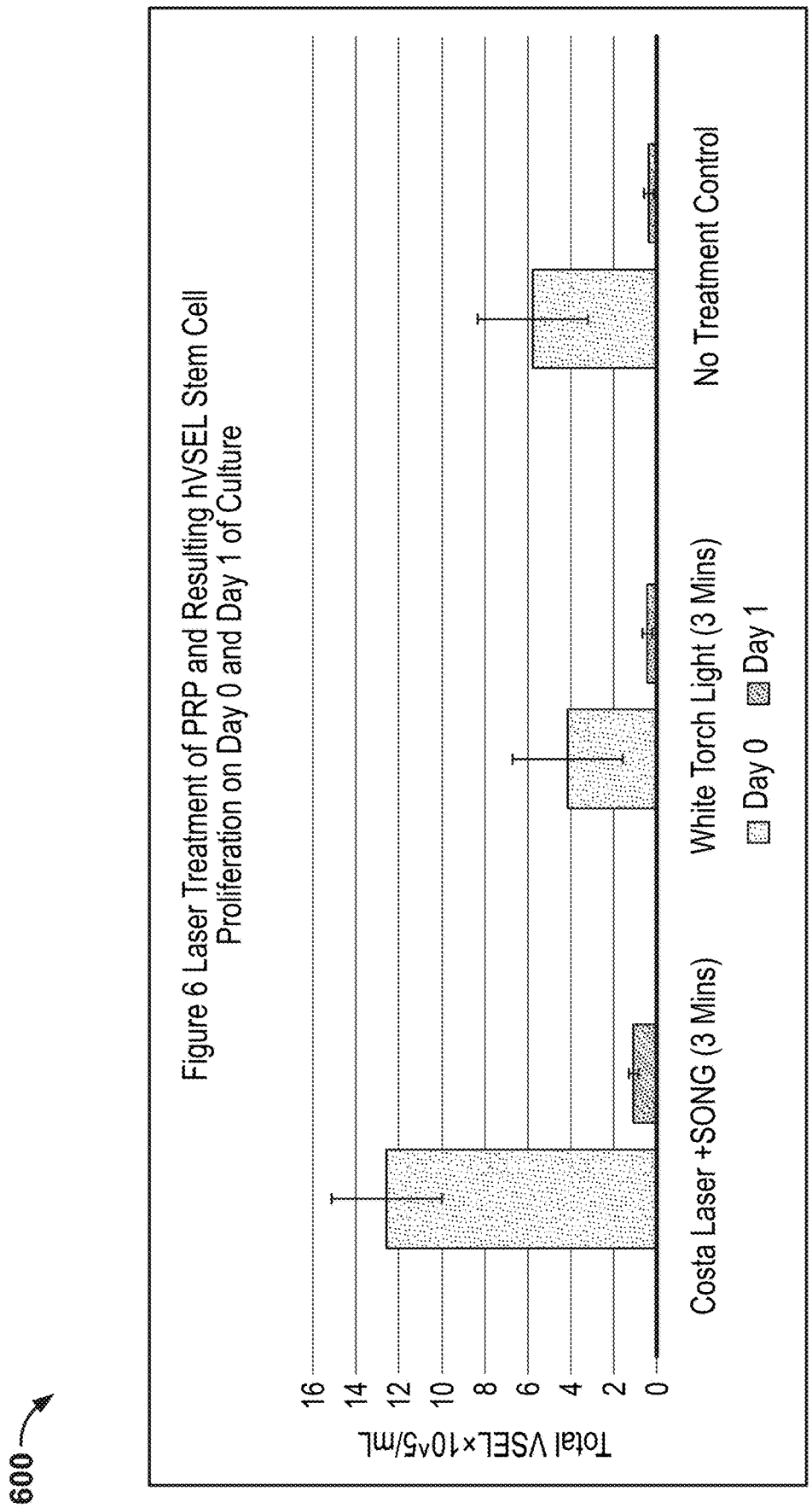
FIG. 6 is a graph illustrating data pertaining to Costa laser+SONG modulation of PRP, related controls and in vitro culture for one day.

FIG. 6 is a graph 600 illustrating data on Costa laser +SONG modulation of PRP, related controls, and in vitro culture for a duration of one day. As shown, when PRP is treated with laser light +SONG for 3 minutes, and analyzed by flow cytometry immediately afterwards, the number of hVSEL stem cells are $1.256 \times 10^6$/mL. The same batch of PRP treated with white torch light for 3 minutes (as a first control) and analyzed immediately contains $4.15 \times 10^5$/mL hVSEL stem cells. The same batch of PRP, undergoing no treatment (as a second control), contains $5.77 \times 10^5$/mL hVSEL stem cells. The mean of these two control samples is $4.96 \times 10^5$/mL. The laser exposed PRP therefore showed a 2.5× (2.5 fold) increase in hVSEL stem cell numbers compared to the mean of the two control groups. This is a rapid effect in that following modulated laser exposure the cells are taken immediately for analysis on the flow cytometer. The time from modulated laser exposure to flow cytometry analysis is therefore no greater than 30 minutes in any of the studies. This observation compares favorably with the clinical use and clinical trial of modulated laser exposed hVSEL in PRP which often show rapid clinical improvements following intravenous infusion of autologous laser exposed hVSEL stem cells in PRP. This is the first time that these laboratory observations and clinical data have been correlated.

In embodiments, it should be noted that the PRP may be treated with laser light +SONG for a predefined time period ranging from 1 minute to 5 minutes, and preferably 3 minutes. In embodiments, the treated platelet rich plasma has an amount of stem cells ranging from $0.5 \times 10^6$/mL to $2.0 \times 10^6$/mL when analyzed immediately after the predefined period of time. In embodiments, the number of hVSEL stem cells after treatment is $1.256 \times 10^6$/mL.

On day 1 of culture in vitro (that is, following 24 hours culture in vitro), the Costa laser+SONG treated PRP contains $1.086 \times 10^5$/mL hVSEL stem cells. On day 1 of culture in vitro, the White Torch light PRP (a first control) contained $0.448 \times 10^5$/mL hVSEL stem cells. On day 1 of culture in vitro the Control PRP (no treatment and a second control) contained $0.376 \times 10^5$/mL hVSEL stem cells. The mean of these two control groups is $0.432 \times 10^5$/mL. The laser exposed PRP after 24 hours in vitro showed a 2.5× (2.5-fold) increase of hVSEL stem cells over the control cells indicating that even though the actual cell counts decreased (which is to be expected following culture in vitro), the ratio of laser modulated hVSEL stem cells to control hVSEL stem cells remained the same over 24 hours. In embodiments, stem cell administration occurs in a time frame ranging from within 1 minute to 24 hours of preparation/laser modulation. In embodiments, stem cell administration occurs in a time frame ranging from within 1 minute to 2 hours of preparation/laser modulation. In embodiments, stem cell administration preferably occurs within 30 minutes of preparation/laser modulation.

These data have confirmed that the laser has a proliferative effect on hVSEL stem cells in PRP. This effect is maintained in relative terms for at least 24 hours in vitro post laser exposure. In embodiments, stem cell administration may occur in a time frame wherein the measurable effect on hVSEL remains post laser exposure, wherein said time may vary depending on a plurality of conditions.

Laser Treatment (Using Magna Costa Laser) of hVSEL Stem Cells in PRP with Titration of Laser Exposure Time and ±SONG Modulation at Day 0 and Day 5

In an embodiment, the hVSEL stem cells in PRP were treated with the Magna Costa laser to assess the numbers of hVSEL present in PRP following laser exposure from 1-3 minutes with and without the SONG modulation in order to confirm optimum settings for clinical use. As described earlier in this specification, the Magna Costa laser is the same as the Costa except for an adjustable wave form. This enables the use of a possibly improved control of a 'flat' wave in these experiments.

In this embodiment, the SONG modulation was set at 60% OPC and all cells are analyzed at Day 0 and then cultured in vitro for 5 days to assess the persistence of any proliferative changes in hVSEL.

Figure 7:
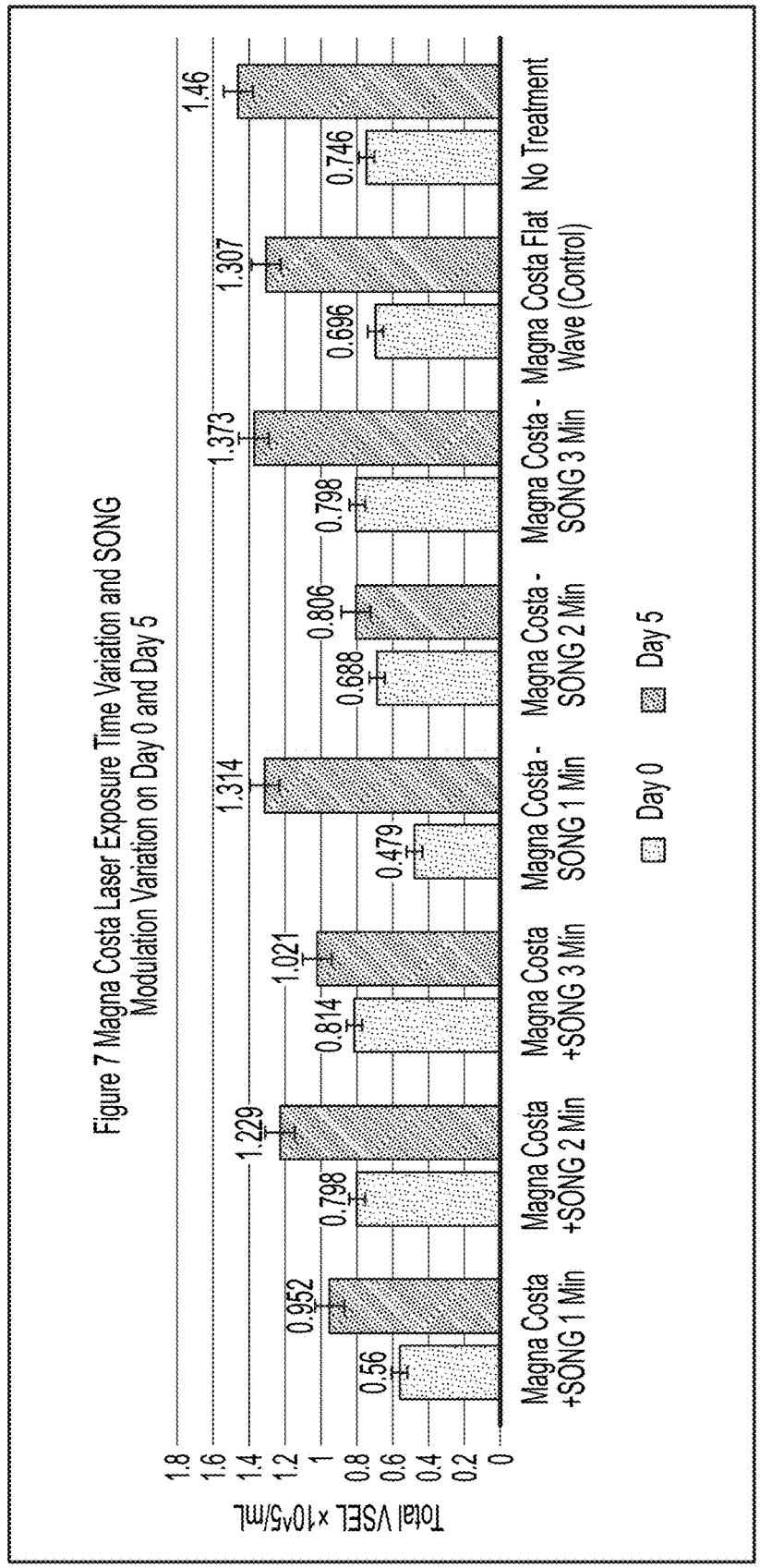
FIG. 7 is a graph illustrating data pertaining to Magna Costa Laser exposure time variation and SONG modulation variation on Day 0 and Day 5.

The purpose of this embodiment is to assess the laser exposure time and the application of SONG modulation, or no SONG modulation, on the proliferation of hVSEL stem cells in PRP on the day of laser exposure (D0) and after five days in vitro (D5). The laser exposure times and SONG modulation are critical to successful hVSEL stem cell proliferation. FIG. 7 is a graph 700 illustrating data pertaining to Magna Costa Laser exposure time variation and SONG modulation variation on day 0 and day 5. In embodiments, the laser exposure time ranges from 1 minute to 6 minutes. In embodiments, the laser exposure time ranges from 1 minute to 3 minutes. In embodiments, for a volume ranging from 20 milliliters to 30 milliliters, the laser exposure time is 3 minutes. In other embodiments, laser exposure time is dependent on the volume of PRP. In other embodiments, laser exposure time is dependent on the quality of harvested PRP.

As shown, on day 0 (the day when the PRP was prepared and lasered) the total number of hVSEL stem cells in the PRP increased as the laser exposure time was increased (from 1 minute to 3 minutes) and the SONG modulation was present throughout. The 2-minute and 3-minute laser exposure time produced very similar numbers of hVSEL stem cells. There was a similar but less pronounced rise in hVSEL stem cell numbers when the laser was applied without SONG modulation. The flat wave and no treatment controls remained similar, noting that the flat wave laser exposure time was 3 minutes.

Thus, in the PRP exposed to the SONG modulated Magna Costa laser for 1-minute, 2-minutes and 3-minutes the numbers of hVSEL stem cells are highest in the 2-minute and 3-minute treatments. In the Magna Costa laser without SONG modulation there are fewer hVSEL stem cells than in the laser SONG modulated group over 1, 2 and 3 minutes but there is a steady increase in detected hVSEL stem cells across the laser exposure times. The SONG modulated Magna Costa flat wave and no treatment controls (hVSEL numbers) are lower than the equivalent SONG modulated laser cell counts at 2-minute and 3-minute laser exposure.

On day 5 of culture in vitro the SONG modulated laser group show increased numbers of hVSEL stem cells compared to Day 0 with slightly more hVSEL stem cells present in the 2-minute and 3-minute laser exposure time. The 1-minute and 3-minute laser exposure without SONG modulation contains more hVSEL stem cells than the 2-minute laser exposure and the flat wave and no treatment controls also contain more hVSEL stem cells overall than in Day 0.

Thus, the day 5 hVSEL stem cell counts, after 5 days culture in vitro, all showed an increase in hVSEL stem cells compared to Day 0. There is also an increase in the control groups which appeared greater than the experimental groups. This anomaly needs further investigation because it could be a true reflection of in vitro proliferation of hVSEL stem cells or it may just be an anomaly in this particular embodiment. In general terms when lasered hVSEL stem cells are cultured in vitro then a reduction in cell numbers is observed.

Costa Laser Treatment (±SONG Modulation) of hVSEL Stem Cells in PRP at Day 0, Day 1 and Day 7

In an embodiment, the PRP (prepared in accordance with the method of FIG. 3) is exposed to the Costa laser for 3 minutes with SONG modulation and 3 minutes without SONG modulation. The resultant PRP is then assessed for hVSEL proliferation and then put into in vitro culture for 1 and 7 days. Cultures are harvested on Day 1 and Day 7 and the resultant cell harvest is assessed for hVSEL proliferation using flow cytometry. This embodiment also includes an assessment of hVSEL numbers in whole peripheral blood following red cell lysis.

This embodiment is directed towards assessing the numbers of hVSEL stem cells in PRP on the day of laser treatment and at Day 1 and Day 7 culture of the cells in vitro and to assess the effect of laser treatment with and without SONG modulation. A measurement is made on the number of hVSEL stem cells in peripheral blood without any treatment. This involved red cell lysis followed by flow cytometry.

Figure 8:
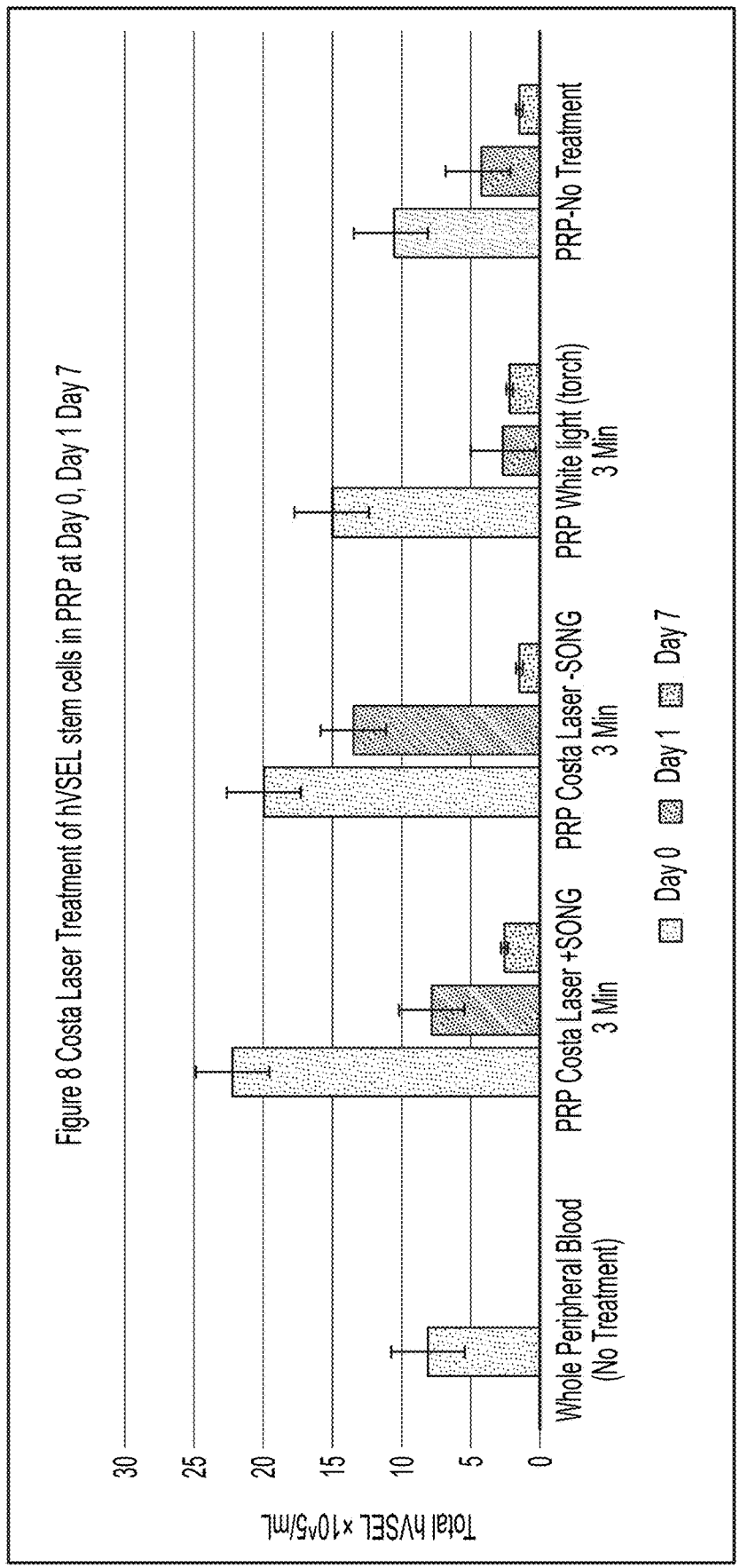
FIG. 8 is a graph illustrating data pertaining to Costa Laser treatment of hVSEL stem cells in PRP at Day 0, Day 1, and Day 7.

FIG. 8 shows a graph 800 illustrating data pertaining to Costa Laser treatment of hVSEL stem cells in PRP at Day 0, Day 1 and Day 7. The number of hVSEL stem cells in this sample of peripheral blood is $8.1 \times 10^5$/mL which correlates well with previous estimates of hVSEL stem cells in PRP at $1 \times 10^6$/mL and the hVSEL stem cells in PRP control in this study of $1.072'10^6$/mL. It is to be expected that PRP will have slightly higher hVSEL stem cell counts than peripheral blood as hVSEL stem cells are concentrated in PRP.

The number of hVSEL stem cells in PRP following 3 minutes of SONG modulated laser treatment is increased to $2.22 \times 10^6$/mL, on Day 1 of culture it is $7.82 \times 10^5$/mL and on day 7 of culture it is $2.56'10^5$/mL. The number of hVSEL stem cells in PRP following 3 minutes of unmodulated laser treatment is increased to $1.994 \times 10^6$/mL, on Day 1 of culture it is $1.348 \times 10^6$/mL and on day 7 of culture it is $1.48 \times 10^5$/mL.

The number of hVSEL stem cells in PRP following 3 minutes of white light treatment is increased to $1.504 \times 10^6$/mL, on Day 1 of culture it is $2.66 \times 10^5$/mL and on day 7 of culture it is $2.18 \times 10^5$/mL. The number of hVSEL stem cells in PRP following no treatment (as a control) is $1.072 \times 10^6$/mL, on Day 1 of culture it is $4.7 \times 10^5$/mL and on day 7 of culture it is $1.657 \times 10^5$/mL.

This embodiment confirms the presence of hVSEL stem cells in whole peripheral blood after red cell lysis. The data shows an increase in hVSEL stem cell numbers in PRP which confirms that PRP is an efficient route to isolate hVSEL stem cells for experimental and clinical use.

The highest numbers of hVSEL stem cells in PRP are found in the Costa laser with SONG modulation with a 3-minute exposure time. The same laser exposure without SONG modulation show fewer hVSEL stem cells but still increased levels over controls indicating some possible benefits of laser exposure even without SONG modulation. The white light and no treatment controls both show fewer hVSEL stem cells than the SONG modulated and SONG unmodulated treatments.

The numbers of hVSEL stem cells present after 1 and 7 days of culture in vitro decreased which may reflect cell death related to in vitro culture.

Time Titration of SONG Modulated Magna Costa and Costa Laser on hVSEL Stem Cells in PRP In an embodiment, the PRP (prepared in accordance with the method of FIG. 3) is exposed to the Magna Costa laser for 3 minutes and the Costa laser for 3, 6 and 9 minutes. White light and no treatment controls are used. hVSEL stem cell flow cytometer analysis is thereafter carried out for all exposure times.

This embodiment is directed towards identifying the optimum laser exposure time for the proliferation of hVSEL stem cells in PRP. FIG. 9 shows a graph 900 illustrating data pertaining to time titration of SONG modulated Magna Costa and Costa Laser on hVSEL Stem Cells in PRP. In embodiments, the laser exposure time ranges from 1 minute to 6 minutes. In embodiments, the laser exposure time ranges from 1 minute to 3 minutes. In embodiments, for a volume ranging from 20 milliliters to 30 milliliters, the laser exposure time is 3 minutes. In other embodiments, laser exposure time is dependent on the volume of PRP. In other embodiments, laser exposure time is dependent on the quality of harvested PRP. As shown, the total hVSEL stem cells found in PRP exposed to the SONG modulated Costa Magna and the Costa laser for three minutes are higher than exposure to the SONG modulated Costa laser for 6 or 9 minutes. These data confirm that the optimum laser exposure time to maximize hVSEL stem cell proliferation is 3 minutes. The white light (torch) control and the no treatment control showed hVSEL stem cell numbers less than the 3-minute SONG modulated laser exposure confirming the optimized exposure time to 3 minutes.

Data resulting from various embodiments of the present specification confirm that laser treatment, exposure or modulation of hVSEL stem cells in PRP results in hVSEL stem cell proliferation. This has a great potential in future routine therapy and also in understanding the true nature of hVSEL stem cells.

In embodiments, optimization of a PRP preparation for laser activation of hVSEL stem cells is dependent upon many factors, including, but not limited to centrifugation time, cell collection, the time between laser treatment and patient administration. In addition, in embodiments, a triple shake method may be employed which may a) result in an increase in the yield of the cells which are concentrated at the interface between the plasma and the gel that effectuates the separation, as fewer cells are lost by virtue of being stuck to the interface and b) an increase in cytokines and growth factors that are present in the preparation either before or after laser treatment.

Unblocking CXCR4 Making it Available for Binding

Endogenous Peptide Inhibitor X4 (EPI-X4) is the antagonistic ligand of CXCR4. This naturally occurring peptide, originating from the fragmentation of albumin, binds to the CXCR4 antigen mostly by interacting in the minor pocket of CXCR4 through its N-terminal residues, thereby inhibiting G-protein signaling to the associated cells. There have been several EPI-X4 derivatives reported and their IC50 values show that the N-terminal residues of EPI-X4 are crucial for binding to CXCR4.

It has subsequently been shown that the NTer-IN configuration (N-Terminal of EPI-X4 IN the minor pocket of CXCR4) plays a vital role in CXCR4/EPI-X4 binding. Furthermore, only seven EPI-X4 residues played any significant role in this binding, four of which, all positively charged, interact through the minor pocket of CXCR4.

In addition, the negatively charged EPI-X4 residue L16 (C-terminal Leu) interacting with the CXCR4 residue K271 (Lys) has a de-stabilizing effect. However, chemical elimination of L16 showed little effect on the binding of EPI-X4 to CXCR4, demonstrating that first three salt bridges and hydrogen bond are the major agents of the binding.

The last two of the seven significant interactions, V11 and T15 of EPI-X4 interact with E25 and R30, which comprise the β-strand of CXCR4, also providing some small additional binding stabilization. The chemical elimination of EPI-X4 residue L1 or K7 almost completely abolishes receptor binding.

Salt bridges are interactions, electrostatic combined with hydrogen bonding, between oppositely charged residues. Whereas hydrogen bonds can combine, as in water, to create a major force, individual bonds are weak and easily broken. The distance between the residues participating in a salt bridge is important and is typically on the order of <400 picometers (pm). Amino acids greater than this distance apart do not qualify as forming a salt bridge and salt bridges experience thermal fluctuations which continuously break and reform the hydrogen bonds.

EPI-X4, originating from albumin fragmented in the acidic conditions of embryonic gastrulation, binds to and dysregulates the CXCR4 expressed by the hVSEL stem cells, protecting the salt bridges and hydrogen bonds in the minor pocket of CXCR4 from thermal fluctuations, thereby maintaining hVSEL stem cell quiescence.

CXCR4 is unblocked by SONG modulated laser light to make it readily available for binding by flow cytometry antibodies. The SONG modulated red laser penetrates the minor pocket of CXCR4 and thus disrupts the hydrogen bonds and salt bridges binding CXCR4 to EPI-X4. A three-minute exposure time to SONG modulated laser is observed to be most effective in unblocking CXCR4. In the given time, the laser thermal turbulence in the minor pocket of CXCR4 maximizes the proliferation of hVSEL stem cells in vitro. In three minutes, the binding of EPI-X4 to CXCR4 is broken and the laser becomes ineffective because the thermal energy of the minor pocket is comparable to that of the red-energy laser.

After three minutes of continuous laser exposure, a new thermal stability is established as the turbulent conditions subside and new hydrogen bonds, if not salt bridges, develop in the hotter but now-stabilizing conditions. When the laser is applied for six and nine minutes, the hVSEL count decreases as the hotter stabilizing conditions in the minor pocket of CXCR4 allow some new hydrogen bonds, which demonstrably show some re-binding effect across the CXCR4/EPI-X4 complex.

The apparent rapid proliferation of hVSEL stem cells in PRP in vitro demonstrates that the SONG modulated red laser for three minutes penetrates into the minor pocket of CXCR4 and interrupts the salt bridges and the hydrogen bonds, thus breaking the CXCR4/EPI-X4 binding and exposing CXCR4 to labelled antibodies in the subsequent flow cytometry analysis.

Intrinsic Age Reduction

Intrinsic epigenetic age (IEA) is a true indicator of biological age at the DNA level. In one embodiment, by using the treatment and administration procedures described herein, in one embodiment, a single treatment, as described herein, can yield a reduction in an individual's IEA by 2 to 4 years, a second treatment can yield an additional reduction in an individual's IEA by 2 to 4 years, a third treatment can yield an additional reduction in an individual's IEA by 2 to 4 years, and a fourth treatment can yield an additional reduction in an individual's IEA by 2 to 4 years. Accordingly, for each treatment, the IEA may reduce by 2 years to 4 years such that four treatments, spread over a period of 1 month to 24 months can yield a reduction in an individual's IEA by 8 to 16 years. By way of another example, in using the treatment and administration procedures as described herein, an individual's IEA may be decreased in a range of 1 year to 4 years. More specifically, in one embodiment, a single treatment, as described herein, can yield a reduction in an individual's IEA by 1 to 4 years, a second treatment can yield an additional reduction in an individual's IEA by 1 to 5 years, a third treatment can yield an additional reduction in an individual's IEA by 1 to 5 years, and a fourth treatment can yield an additional reduction in an individual's IEA by 1 to 5 years. Accordingly, for each treatment, the IEA may reduce by 1 year to 5 years such that four treatments, spread over a period of 1 month to 24 months can yield a reduction in an individual's IEA by 4 to 20 years. In embodiments, treatments are administered every week to every year and in any increment therein. In embodiments, treatments are administered every week to every six months and in any increment therein. Optionally, treatments may be administered in any frequency as long as it achieves the objectives of the present specification.

In embodiments, a patient experiences a decrease in biological age in a range of 1 year to 4 years based on a first administration of the treated platelet rich plasma. In embodiments, a patient experiences a decrease in biological age in a range of 4 years to 9 years based on a second administration of the treated platelet rich plasma. In embodiments, the second administration of the treated platelet rich plasma occurs 1 week to 6 months after the first administration.

Figure 10A:
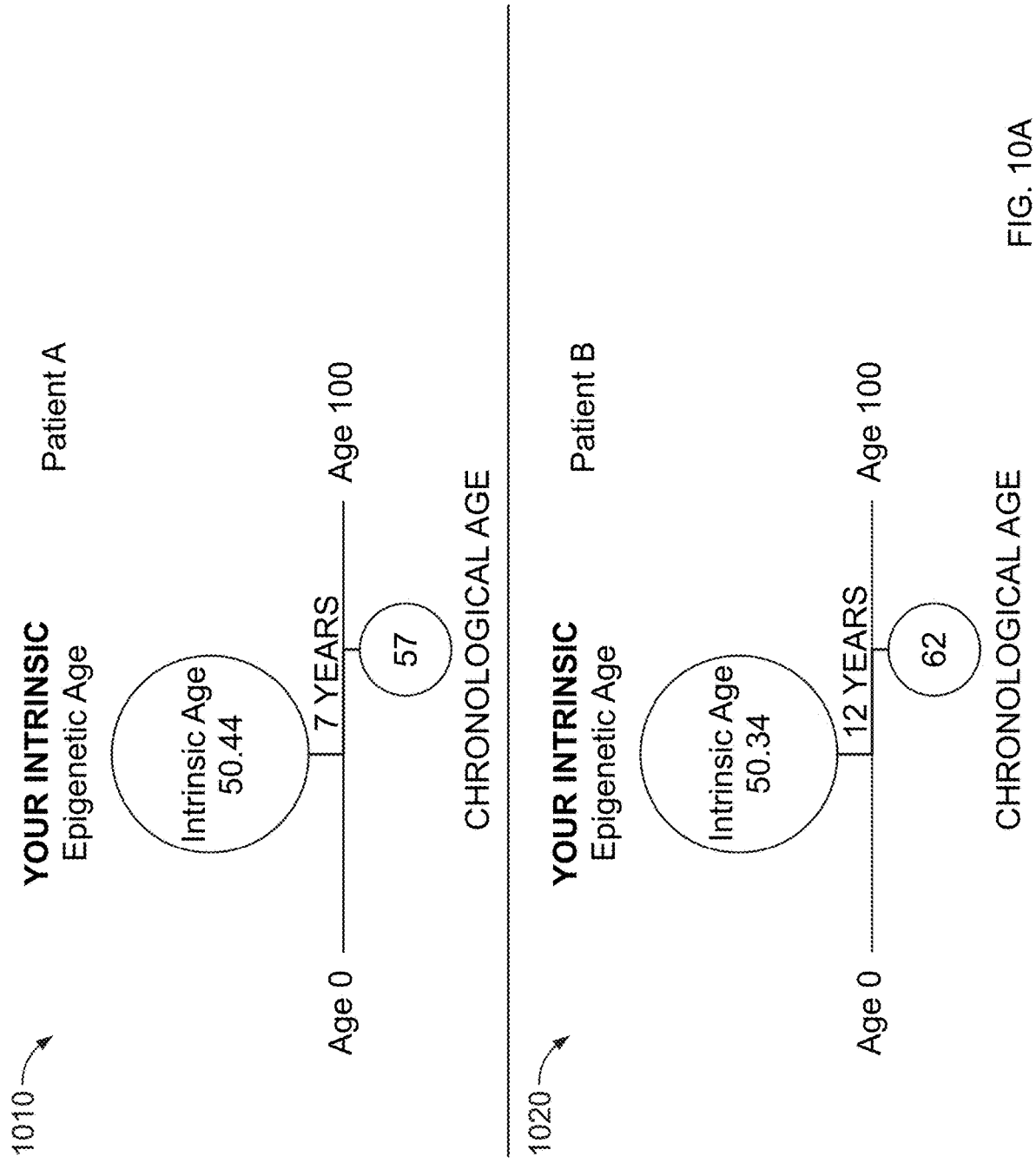
FIG. 10A illustrates an intrinsic epigenetic age (IEA) of two patients.
Figure 10B:
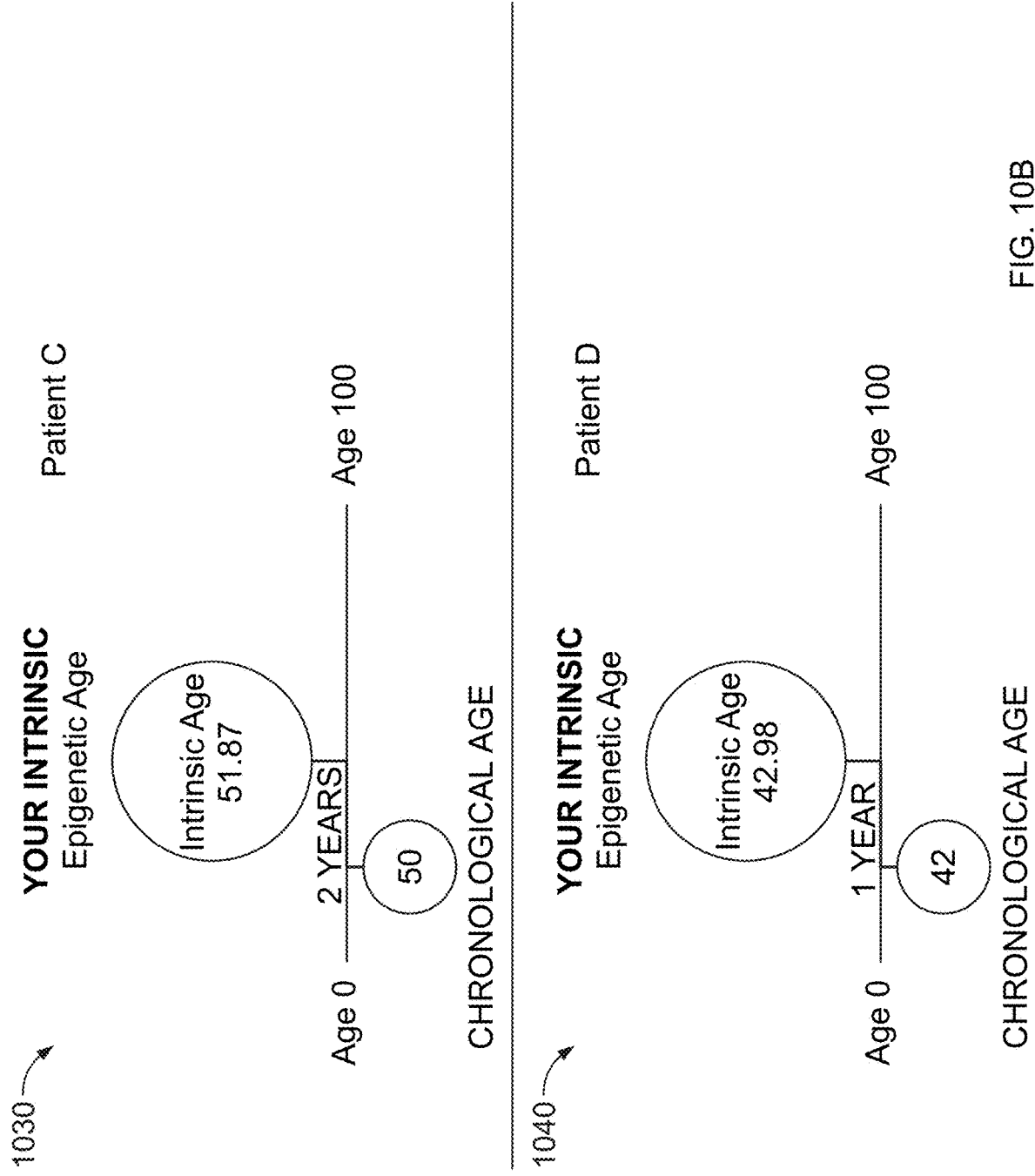
FIG. 10B illustrates an IEA of another two patients.
Figure 10C:
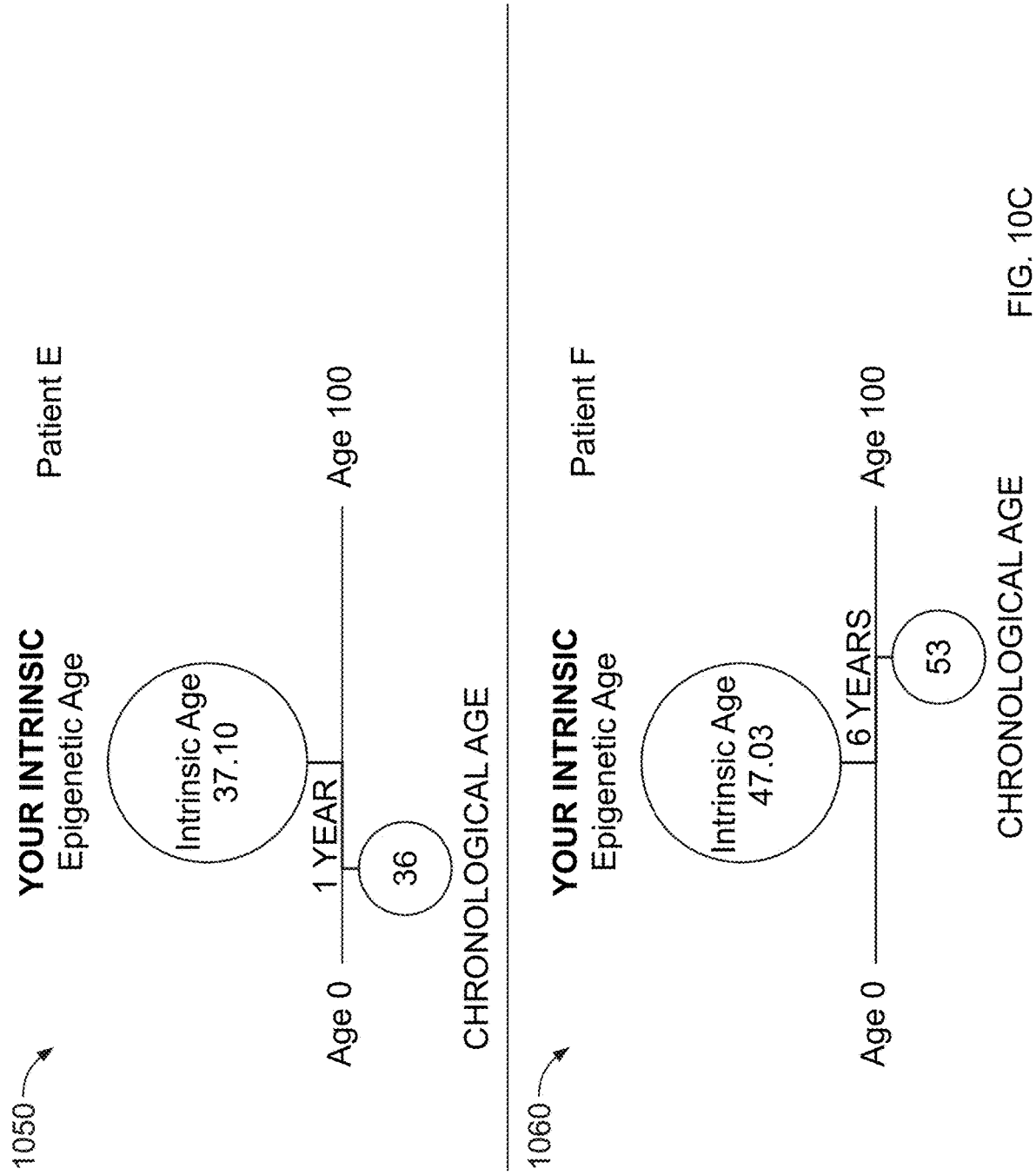
FIG. 10C illustrates an IEA of yet another two patients.

Referring to FIGS. 10A to 10D, examples of intrinsic epigenetic ages determined for eight different humans, referred to as patient A through patient H, are provided. FIG. 10A shows an IEA of patient A 1010 at 50.44 years when patient A's chronological age is 57 years. The figure also illustrates an IEA of patient B 1020 at 50.34 years, when patient B's chronological age is 62 years. FIG. 10B shows an IEA of patient C 1030 at 51.87 years, when patient C's chronological age is 50 years. The figure also illustrates an IEA of patient D 1040 at 42.98 years, when patient D's chronological age is 42 years. FIG. 10C shows an IEA of patient E 1050 at 37.10 years, when patient E's chronological age is 36 years. The figure also illustrates IEA of patient F 1060 at 47.03 years, when patient F's chronological age is 53 years. FIG. 10D shows an IEA of patient G 1070 at 63.41 years, when patient G's chronological age is 66 years. The figure also illustrates an IEA of patient H 1080 at 50.62 years, when patient H's chronological age is 50 years.

Therefore, chronological age can be very different from the biological age, which can further be different for IEA and EEA.

Figure 11:
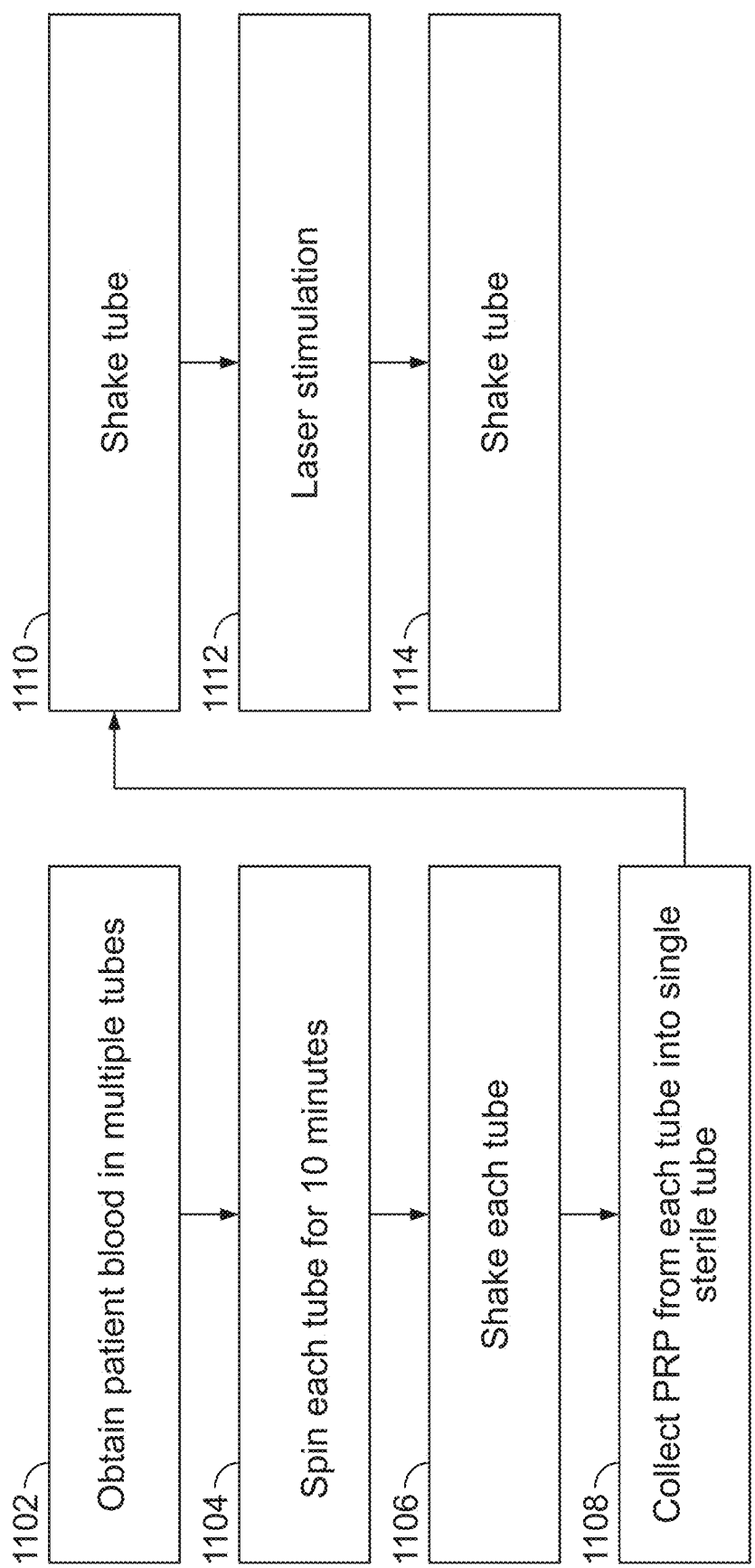
FIG. 11 is a flow chart illustrating an exemplary process of preparing PRP that contains hVSEL stem cells, which are used for reducing IEA, in accordance with some embodiments of the present specification.

It is desirable to reduce the speed of, inhibit, or even reverse epigenetic aging in general, and IE aging, in particular. To do so, a treatment as shown in FIG. 11 is administered to each patient. FIG. 11 is a flow chart illustrating an exemplary process of preparing PRP that contains hVSEL stem cells, which are used for reducing IEA, in accordance with some embodiments of the present specification. IEA is reduced by increasing regenerative growth factors resulting from proliferation of hVSEL stem cells. At step 1102, a patient's blood is obtained in a plurality of tubes of 10 cc each. In embodiments, the number of tubes ranges from 3 to 12. In a preferred embodiment, a patient's blood is obtained in six tubes of 10 cc each. At step 1104, each tube is spun with a centrifugal G-force of approximately 270 G for approximately 10 minutes. The spinning process pulls red/white blood cells into a gel at the bottom of each tube. Platelets, hVSEL stem cells, and plasma remain separated above the gel in the form of PRP. Based on basic density distribution, an upper third of the PRP has the lowest concentration of hVSEL stem cells, while a bottom third of PRP, near the gel interface, has the highest concentration of hVSEL stem cells. At step 1106, the tubes are shaken for a first time. The shaking involves gently rocking the tube in a back-and-forth motion for approximately 10 seconds. The motion knocks loose hVSEL stem cells in PRP near the gel boundary, thereby improving hVSEL yield by at least 1% compared to an identical procedure where no such shaking is performed. At step 1108, approximately 6 to 7 cc of PRP per tube is harvested. The harvested amounts are collected in a separate sterile tube. At step 1110, the tube containing the PRP harvested at step 1108 is shaken (second shaking). In some embodiments, the shaking is performed vigorously for approximately 20 seconds to release regenerative factors. At step 1112, laser stimulation is applied. Laser stimulation is applied as described above. In some embodiments, SONG modulated laser stimulation is applied for three minutes. At step 1114, the tube is shaken for a third time to awaken dormant hVSEL stem cells and get cytokines and growth factors from hVSEL stem cells.

FIG. 11 provides an exemplary process of treating PRP obtained from blood samples of a patient. Variations to the process without deviating from the scope of the present invention are also possible to reduce IEA. Reduction in biological age may increase on a per treatment basis. The treatment described in FIG. 11 is repeated to achieve additional reductions in the biological age. Therefore, in an example, one treatment may decrease biological age by one year while an additional treatment may decrease it by an additional year. The amount of reduction in IEA achieved by embodiments of the present specification is higher than any other known treatment.

Accordingly, referring back to the case examples provided in FIGS. 10A to 10D, if patient A is provided one treatment, the chronological age reduces from 50.44 years to approximately 48 to 46 years old. If patient B is provided two treatments, spread apart by a time period ranging from 1 week to 6 months, the chronological age reduces from 50.34 years to approximately 46 to 42 years old. If patient C is provided three treatments, each spread apart by a time period ranging from 1 week to 6 months, the chronological age reduces from 51.87 years to approximately 46 to 40 years old. If patient D is provided four treatments, each spread apart by a time period ranging from 1 week to 6 months, the chronological age reduces from 52.98 years to approximately 45 to 37 years old. If patient E is provided five treatments, each spread apart by a time period ranging from 1 week to 6 months, the chronological age reduces from 37.10 years to approximately 27 to 17 years old. If patient F is provided six treatments, each spread apart by a time period ranging from 1 week to 6 months, the chronological age reduces from 47.03 years to approximately 35 to 23 years old. Finally, if patient G is provided seven treatments, each spread apart by a time period ranging from 1 week to 6 months, the chronological age reduces from 63.41 years to approximately 49 to 35 years old.

The above examples are merely illustrative of the many applications of the system of present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method of administering treated platelet rich plasma to a patient comprising:
   proliferating stem cells of the patient, wherein the proliferation comprises preparing platelet rich plasma containing stem cells and treating the platelet rich plasma containing stem cells with modulated pulses of laser light having a predefined wavelength and for a predefined period of time; and,
   administering the treated platelet rich plasma to the patient,
   wherein preparing and treating the platelet rich plasma comprises:
   adding the patient's blood into a plurality of one or more tubes;
   centrifuging the one or more tubes to produce the platelet rich plasma; and
   aliquoting the produced platelet rich plasma into a sterile tube,
   wherein the centrifuging the one or more tubes further comprises shaking the one or more tubes after centrifuging the one or more tubes, and
   wherein the aliquoting the produced platelet rich plasma into a sterile tube further comprises shaking the sterile tube after aliquoting the produced platelet rich plasma, and
   wherein the treating the platelet rich plasma containing stem cells with modulated pulses of laser light further comprises shaking the platelet rich plasma after treating the platelet rich plasma containing stem cells with modulated pulses of laser light.

2. The method of claim 1, wherein
   the centrifuging the plurality of one or more tubes is conducted at a predefined g force for a predefined period of time to produce the platelet rich plasma.

3. The method of claim 1, wherein the shaking the plurality of tubes after centrifuging the one or more tubes comprises a plurality of tubes.

4. The method of claim 1, wherein the treatment of the platelet rich plasma is carried out in white torch light.

5. The method of claim 1, wherein the predefined wavelength has a value that lies within a range of 300 nm to 1000 nm.

6. The method of claim 1, wherein the predefined wavelength is 670 nm.

7. The method of claim 1, wherein the predefined period of time has a value that lies within a range of 1 minute to 5 minutes.

8. The method of claim 1, further comprising analyzing said treated platelet rich plasma immediately after the predefined period of time, wherein, when said treated platelet rich plasma is analyzed immediately after the predefined period of time, said treated platelet rich plasma has an amount of stem cells that varies within a range of $0.5 \times 10^6$/mL to $2.0 \times 10^6$/mL.

9. A method of reducing an intrinsic epigenetic age administering treated platelet rich plasma to a patient comprising:
   proliferating stem cells of the patient, comprising:
      adding normal human blood into a plurality of tubes, wherein normal human blood is defined as blood in a chemical and physical state as when immediately withdrawn from a human and without any further processing;
      centrifuging the plurality of tubes at a predefined g force for 10 minutes to produce platelet rich plasma;
      shaking the plurality of tubes;
      aliquoting the produced platelet rich plasma into a sterile tube;
   shaking the platelet rich plasma in the sterile tube;
   treating the platelet rich plasma with modulated pulses of laser light having a predefined wavelength and for a predefined period of time; and
   shaking the treated platelet rich plasma; and,
      administering the treated platelet rich plasma to the patient.

10. The method of claim 9, wherein the treatment of the platelet rich plasma is carried out in white torch light.

11. The method of claim 9, wherein the predefined wavelength has a value that lies within a range of 300 nm to 1000 nm.

12. The method of claim 9, wherein the predefined wavelength is 670 nm.

13. The method of claim 9, wherein the predefined period of time has a value that lies within a range of 1 minute to 5 minutes.

14. The method of claim 9, further comprising analyzing the treated platelet rich plasma immediately after the predefined period of time, wherein, when the treated platelet rich plasma is analyzed immediately after the predefined period of time, the treated platelet rich plasma has an amount of stem cells that varies within a range of $0.5 \times 10^6$/mL to $2.0 \times 10^6$/mL.

15. The method of claim 9, wherein the treated platelet rich plasma exhibits a 2.5 fold increase in stem cells compared to a mean of an amount of stem cells in a same volume of first and second control samples, wherein the first control sample includes the platelet rich plasma treated with white torch light for the predefined period of time, and wherein the second control sample includes the platelet rich plasma without any light treatment.

16. The method of claim 9, wherein the modulation cancels a central wavelength band of the laser light such that the remaining upper and lower wavelength bands create a beat frequency pattern of sparse nodes.

* * * * *